(12) United States Patent
Weisleder et al.

(10) Patent No.: US 8,420,338 B2
(45) Date of Patent: Apr. 16, 2013

(54) SERUM MG53 AS A DIAGNOSTIC MARKER FOR TISSUE INJURY

(75) Inventors: Noah Weisleder, Elizabeth, NJ (US); Jianjie Ma, Belle Mead, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 0 days.

(21) Appl. No.: 13/290,070

(22) Filed: Nov. 5, 2011

(65) Prior Publication Data

US 2012/0115170 A1 May 10, 2012

Related U.S. Application Data

(60) Provisional application No. 61/410,430, filed on Nov. 5, 2010.

(51) Int. Cl.
*G01N 33/53* (2006.01)
*G01N 31/00* (2006.01)

(52) U.S. Cl.
USPC .............. 435/7.21; 435/7.1; 436/1; 436/501; 436/518; 424/9.1; 424/520; 422/1; 422/430; 530/300; 530/350

(58) Field of Classification Search .................. None
See application file for complete search history.

(56) References Cited

U.S. PATENT DOCUMENTS

| | | |
|---|---|---|
| 6,943,241 B2 | 9/2005 | Isogai et al. |
| 7,842,467 B1 | 11/2010 | Heidbrink et al. |
| 7,981,866 B2 | 7/2011 | Ma et al. |
| 2003/0165937 A1 | 9/2003 | Brown et al. |
| 2003/0216424 A1 | 11/2003 | Davis |
| 2003/0236392 A1 | 12/2003 | Isogai et al. |
| 2006/0121496 A1 | 6/2006 | Srivastava et al. |
| 2007/0020637 A1 | 1/2007 | Isogai et al. |
| 2007/0123494 A1 | 5/2007 | Seipelt |
| 2009/0208473 A1 | 8/2009 | Weisleder et al. |
| 2009/0318348 A1 | 12/2009 | Ma et al. |
| 2011/0202033 A1 | 8/2011 | Weisleder et al. |
| 2011/0287004 A1 | 11/2011 | Ma et al. |
| 2011/0287015 A1 | 11/2011 | Ma et al. |

FOREIGN PATENT DOCUMENTS

| | | |
|---|---|---|
| EP | 1440981 | 1/2004 |
| JP | 2003-135075 | 5/2003 |
| WO | WO 2005081911 A2 | 9/2005 |
| WO | WO 2008-054561 | 5/2008 |

OTHER PUBLICATIONS

Cai et al. Membrane repair defects in muscular dystrophy are linked to altered interaction between MG53, caveolin-3, and dysferlin. J. Biol Chem. Jun. 5, 2009. vol. 284. N 23, pp. 15894-15902.
Skolnick et al. From genes to protein structure and function: novel applications of computational approaches in the genomic era. Trends in Biotech 18(1): 34-39, 2000.
Bork, A. Powers and pitfalls in sequence analysis: the 70% hurdle. Genome Res 10: 398-400, 2000.
Doerks et al. Protein annotation: detective work for function prediction. Trends in Genetics 14(6): 248-250, 1998.
Smith et al. The challenges of genome sequence annotation or "The devil is in the details". Nature Biotech 15: 1222-1223, 1997.
Brenner, S.E. Errors in genome function. Trends in Genetics 15(4): 132-133, 1999.
Bork et al. Go hunting in sequence databases but watch out for the traps. Trends in Genetics. 12(10): 425-427, 1996.
Wells. J.A. Additivity of mutational effects in proteins. Biochemistry 29 (37): 8509-8517, 1990.
Ngo et al. Computational complexity, protein structure prediction, and the Levinthal paradox. The Protein Folding Problem and Tertiary Structure Prediction, pp. 492-495, 1994.
Tokuriki et al. Stablility effects of mutations and protein evolvability. Curr Opin Structural Biol 19: 596-604, 2009.
Phillips, A., The challenge of gene therapy and DNA delivery. J Pharm Pharmacology 53: 1169-1174, 2001.
Rubanyi, G.M. The future of human gene therapy. Mol Aspects Med 22: 113-142, 2001.
Juengst, E.T. What next for human gene therapy? BMJ 326: 1410-1411, 2003.
Takeshima, H. Genbank Accession No. AB231474; Apr. 4, 2006; 2 total pages.
Takeshima, H. Genbank Accession No. AB231473; Apr. 4, 2006; 2 total pages.
Extended European Search Report dated Jun. 4, 2012, for EP 08855963.8.
International Search Report dated Apr. 6, 2012, for PCT/US2011/030703.
ISR, Int'l Preliminary Report on Patentability, and Written Opinion of the ISA for PCT/US2008/085573.
International Search Report for PCT/US2007/015815.
Supplementary European Search Report and Opinion for: App. No. EP 07 86 7154.2-1212/2037737; PCT/US2007/015815.
Short, K. M., and Cox, T.C. Subclassification of the RBCC/TRIM Superfamily Reveals a Novel Motif Necessary for Microtubule Binding. JBC v281(13):8970-80, Mar. 31, 2006.
Meroni Germana et al: TRIM/RBCC. A novel class of single protein RING finger E3 ubiquitin Ligases. Bioessays: News and Reviews in Molecular, Cellular and Developmental Biology Nov. 2005, vo1-27, No. 1.1, Nov. 2005, pp. 1147-1157, XP002562734 ISSN:0265-9247.
Bansal Dimple et al:—Dysferlin and the plasma membrane repair in muscular dystrophy. Trends in Cell Biology, vol. 14, No. 4, Apr. 2004, pp. 206-213, XP002562733 ISSN: 0962-8924.
Cai Chuanxi et al: MG53 regulates membrane budding and exocytosis in muscle cells. The Journal of Biological Chemistry Jan. 30, 2009, vol. 284, No. 5, Jan. 30, 2009, pp. 33t4-3322, XP002562735 ISSN: 0021-9258.
Cai Chuanxi et al: MG53 nucleate assembly of cell membrane repair machinery. Nature Cell Biology Jan. 2009, vol. 11, No. L, Jan. 2009, pp. 56-64, XP002562736 ISSN: 1476-4679.
File History of 7,981,866, patent date Jul. 19, 2011.
International Search Report for PCT/US2010/034331.
Cai et al. Biophysical Journal, 2007, Supplement S, pp. 20A-21A.
Coral-Vazquez, R. et al. Disruption of the sarcoglycan-sarcospan complex in vascular smooth muscle: a novel mechanism for cardiomyopathy and muscular dystrophy. Cell 98, 465-74 (1999).

(Continued)

*Primary Examiner* — Lisa Cook
(74) *Attorney, Agent, or Firm* — McCarter & English, LLP

(57) ABSTRACT

Disclosed herein are compositions and methods for measuring the level of MG53 found in a biological fluid as a biomarker for a disease or disorder, e.g., tissue damage, exercise capacity or a muscle-related disease or disorder. In addition, the invention relates to targeting the native MG53 found in the blood as a therapeutic approach.

20 Claims, 7 Drawing Sheets

OTHER PUBLICATIONS

Doherty, K. R. & McNally, E. M. Repairing the tears: dysferlin in muscle membrane repair. Trends Mol Med 9, 327-30 (2003).

Kudryashova, E., Kudryashov, D., Kramerova, I. & Spencer, M. J. Trim32 is a ubiquitin ligase mutated in limb girdle muscular dystrophy type 2H that binds to skeletal muscle myosin and ubiquitinates actin. J Mol Biol 354, 413-24 (2005).

Miyake, K. & McNeil, P. L. Vesicle accumulation and exocytosis at sites of plasma membrane disruption. J Cell Biol 131, 1737-45 (1995).

Perez-Caballero, D., Hatziioannou, T., Yang, A., Cowan, S. & Bieniasz, P. D. Human tripartite motif 5alpha domains responsible for retrovirus restriction activity and specificity. J Virol 79, 8969-78 (2005).

Reymond et al., May 1, 2001, EMBO J, 20(9): 2140-2151.

Tsutsumi et al. Cardiac-specific expression of caveolin-3 induces endogenous cardiac protection by mimicking cardiac ischemic preconditioninng circulation. Nov. 4, 2008 118(19): 1979-88.

XP002562730: Database Geneseq [Online] Oct. 7, 2004, xP002562730 retrieved from EBI accession No. GSP:ADQ67780.

XP002562731: Database EMBL [Online] Apr. 4, 2006, 0ryctolagus cuniculus MG53 mRNA for mitsugumin 53, complete cds. xP002562731 retrieved from EBI accession No. EMBL: AB231473.

XP002562732: Database EMBL [Online] Apr. 4, 2006, Mus musculus MG53 mRNA f or mitsugumin 53, complete cds. xP002562732 retrieved from EBI accession No. EMBL: AB231474, AB231473.

Extended European Search Report for EP 08 85 5963, Apr. 6, 2012.

FIG. 1(CONT.)

```
                     190        200        210        220        230        240
                      |          |          |          |          |          |
Mouse          KMRME ALESG DREAEV GEAGVA RRELS HSYLEQ QMEKV EVADKPQTEF
Rat            KMRME ALESG DREAEV GEAGVA RRELS HSYLEQ QMEKV EVADKPQTEF
Human          KMRVE ALESG DREAEV GEAGVA RRELG HSYLEQ QMEKV EVADKPQTEF
Chimpanzee     KMRVE ALESG DREAEV GEAGVA RRELG HSYLEQ QMEKV EVADKPQTEF
Rhesus         KMRVE ALESG DREAEV GEAGVA RRELG HSYLEQ QMEKV EVADKPQTEF
Canine         KMRVE ALESG DREAEV GEAGVA RRELG HSYLEQ QMEKV EVADKPQTEF
Bovine         KMRLE ALESG DREAEV GEAGVA RRELG HSYLEQ QMEKV EVADKPQTEF
Rabbit         KMRVE ALESG DREAEV GEAGVA RRELG HSYLEQ QMEKV EVADKPQTEF
Opposum        VMRAF ALESG DREAEV GEAGTA YAERR IVTSYLEQ QMEKV EVTSQFQTEF
X. laevis      AMRSY IHEAS DREAES GEAATE LVEEK TSGHYLEK QMEKV DVESQEQTEF
X. tropical    AMRSY IHEAS DREAS NASH TATE LVEEK TSGHYLEQ QMEKV DVESQEQTEF
                 **  **   *****  ***     *  **  *      *****  *****  ****
Prim.cons.                                                              QTEF 250        260        270        280        290        300
                      |          |          |          |          |          |
Mouse          LMKFCLVTSRLQKILSKSPPPARLDIQLPVISDDFKFQVRKEMFRALNFALEELTFDPSS
Rat            LMKFCLVTSRLQKILSKSPPPARLDIQLPVISDDFKFQVRKEMFRALMPALEELTFDPSS
Human          LMKYCLVTSRLQKILSKSPPPARLDIQLPIISDDFKFQVRKEMFRALMPALEELTFDPSS
Chimpanzee     LMKYCLVTSRLQKILASSPPPARLDIQLPIISDDFKFQVRKEMFRALMPALEELTFDPSS
Rhesus         LMKYCLVTSRLQKILASSPPPARLDIQLPIISDDFKFQVRKEMFRALMPALEELTFDPSS
Canine         LMKYCLVTSRLQKILASSPPPARLDIQLPVISDDFKFQVRKEMFRALMPVTKELTFDPSS
Bovine         LMKYCLVTSRLQKILASSPPPARLDIQLPIISDDFKFQVRKEMFRALMPARQELTFDPST
Rabbit         LMKYCLVTSRLQKILASSPPPARLDIQLPIISDDFKFQVRKEMFRALMPALEELTFDPSS
Opposum        LRKYCLVTSRLQKILASSPPAARLDIQLPIISDDFKFQVRKEMFRALMPQMEVLTFDPAG
X. laevis      LRKYCVVAARLNKILSKSPPPGRLDIQLPIISDEFKFQVWRKEMFRAIMPALEKMTFDPDT
X. tropical    LRKYCVVAARLNKILAESPPPGRLDIQLPIISDEFKFQVWRKEMFRAIMPALENLTFDPDT
                 ***  **    * ***  ****  ****** ***  ********** *****     ****
Prim.cons.     LMKYCLVTSRLQKILASSPPPARLDIQLPIISDDFKFQVRKEMFRALMPA 310        320        330        340        350        360
                      |          |          |          |          |          |
Mouse          AHPSLVVSSSGRRVECSEQKAPPAGEDTRQFDKAVAVVAQQLLSQGEHYWEVEVGGKPRW
Rat            AHPSLVVSASGRRVECSEQKAPPAGEDTCQFDKTVAVVAKQLLSQGEHYWEVEVGGKPSW
Human          AHPSLVVSSSGRRVECSEQKAPPAGEDPRQFDKAVAVVAHQQLSEGERYWEVEVSGDKPRW
Chimpanzee     AHPSLVVSSSGRRVECSEQKAPPAGEDPRQFDKAVAVVAHQQLSEGERYWEVEVGDKPRW
Rhesus         AHPGLVVSSSGRRVECSEQKAPPAGEDPRQFDKAVAVVAHQQLSEGERYWEVEVSDKPRW
Canine         AHPSLVLGPSGRRVECSEQKAPPAGEDPCQFDKAVAVVAQQVLSEGERYWEVQVGEKPRW
Bovine         AHPSLVLSNSGRCVECSEQKAPPAGEDPRQFDKAVAVVTIQLLSEGERYWEVEVGDKPRW
Rabbit         AHPSLVVSPTGRRVECSEQKAPPAGEDPRQFDKAVAVVAQQLLSDKERYWEVEVGDKPRW
Opposum        AHPSLLVSPSGRRVECVEQKAPPAGEDPQQFDKAVRLVARQQLSEGERYWEVEVGDKPRW
X. laevis      AQQYLVVSGESK SVECADQRQS-VSDK PNRFDKSNCLVSKQS FTEGE SYWEV IVEDKPSW
X. tropical    AQQNLVVPSDGK SVECSEQRQS-VSDK PNRFDKSNCLVSKES FTEGE SYWEV LVEDKPSW
                **    **    * ***  ***   *    * *    **       ***  ******
Prim.cons.                                                              GDKPRW
```

FIG. 1(CONT.)

```
                        370         380         390         400         410         420
                         |           |           |           |           |           |
Mouse         ALGVMAADASRRGRLHAVPSQGLWLLGLREGKILEAHVEAKPPRALRTPERPPARIGLYL
Rat           ALGVMAADASRRGRLHAVPSQGLWLLGLREGKILEAHVEAKPPRALRTPERPPARIGLYL
Human         ALGVIAASAPRRGRLHAVPSQGLWLLGLREGRILEAHVEAKPPRALRGPERRPTRIGLYL
Chimpanzee    ALGVIAASAPRRGRLHAVPSQGLWLLGLREGRILEAHVEAKPPRALRGPERRPTRIGLYL
Rhesus        ALGVIAASPPRRGRLHAVPSQGLWLLGLREGRILEAHVEAKPPRALRGPERRPTRIGLYL
Canine        ALGVIAAQASRRGRLHAVPSQGLWLLGLREGKILEAHVEAKPPRALRTPERRPTRIGIYL
Bovine        ALGVIGAQAGRRGRLHAVPSQGLWLLGLREGKILEAHVEAKPPRALRTPERRPTRIGIYL
Rabbit        ALGVMASPASRPGRLHAVPSQGLWLLGLREGKTLEAHVEAKPPRALRTPERRPTRIGLYL
Oppossum      GLGLISADVGRPGRLRPTPGQGFWGLGLREGRVYEAHVEGKPPKVLRVDGR-PSRIGLYL
X. laevis     ALGIISETASRRGKLHATPSRGFWLIGCKEGRVYEARTEQKPPKVLRVEGR-PERIGVYL
X. tropical   ALGVISETASRRGKLHASPRRGFWLIGCKEGRVYEARTEQKPPKVLRVEGR-PERIGIYL
                *   *    *  **    **      **    **    ***  *  *    *   *

Prim.cons.    ▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓

430         440         450         460         470         480
                         |           |           |           |           |           |
Mouse         SFADSVLAFYDASNPDVLTPIFSFRERLPGPVTPIPPDVCWHDKGKNAQPLLIVGPE-----QEQA
(Seq Id No 3)
Rat           SFADSVLTPYDASNTDALTPLFSFRERLPGPVTPMPPDVCWHDKGKNAQPLLIVGPE-----SEQA
(Seq Id No 10)
Human         SFGDSVLSFYDASQADALVPLFAFRERLPGPVTPPPDVCWHDKGKNAQPLLIVGPE-----GARA
(Seq Id No 1)
Chimpanzee    SFGDSVLSFYDASQADNLVPLFAFRERLPGPVYPPPDVCWHDKGKNAQPLLIVGPE-----GARA
(Seq Id No 7)
Rhesus        SFGDSVLSFYDASQADALVPLFAFRERLPGPVYPPPDVCWHDKGKNAQPLLIVGPE-----GARA
(Seq Id No 8)
Canine        SFGDSVLSFYDASQPDALELLFAFRERLPGPVTPPPDVCWHDKGKNAQPLLIVGPE-----GERA
(Seq Id No 6)
Bovine        SFGDSVLSFYDASQPDALELLFAFRERLPGPVTPPPDVCWHDKGKNAQPLLIVGPEVDGGSGSSEA
(Seq Id No 5)
Rabbit        SFGDSVLAFYDASQADALELLFAFRERLPGPVYPPPDVCWHDKGKNAQPLLIVGPE-----GQRA
(Seq Id No 3)
Oppossum      SFREGVLSTYDASQLGNLLPLTAFHERLPGPVYPPPDVCWHDKGKNAQPLLILGPE-----SEQ-
(Seq Id No 9)
X. laevis     SFGDSVVSPTDGSQEGNLKLLYTPNERFSGRLAPPTDVCWHDKGKNAQPLKIFYPP-----AEQL
(Seq Id No 11)
X. tropical   SFGDSVVSPTDSSQEGNIKLLYTPNERFSGRLSPPTDVCWHDKGKNAQPLKIFYPP-----AEQL
(Seq Id No 12)
                ** ****  *  *      *    **   *   **  ***********  ***

Prim.cons.    ▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓EVSGSGSEA
(Seq Id No 13)
```

FIGURE 3
a.
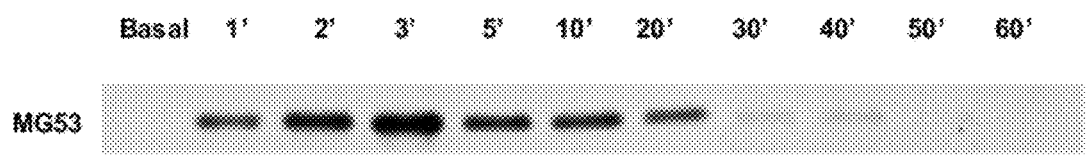
b.
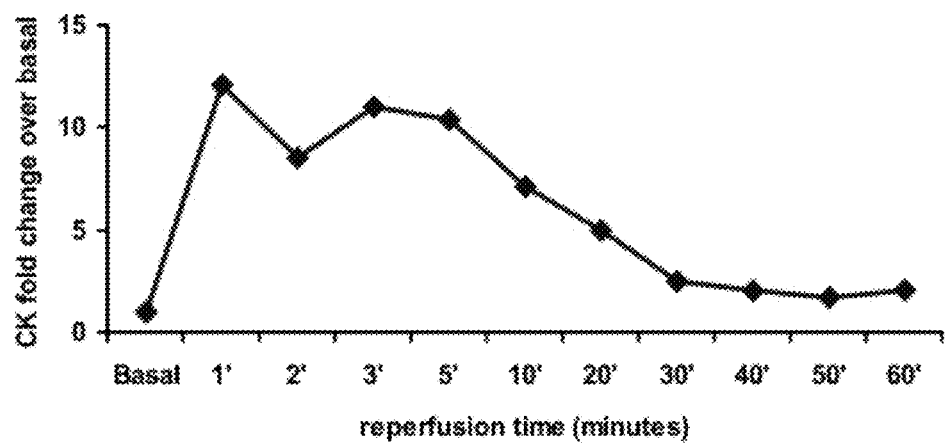

FIGURE 5
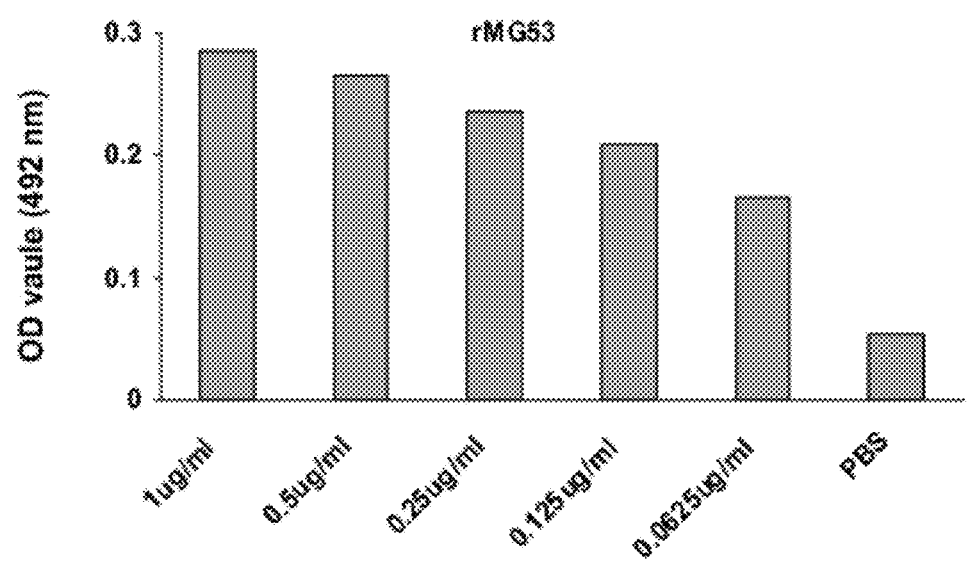
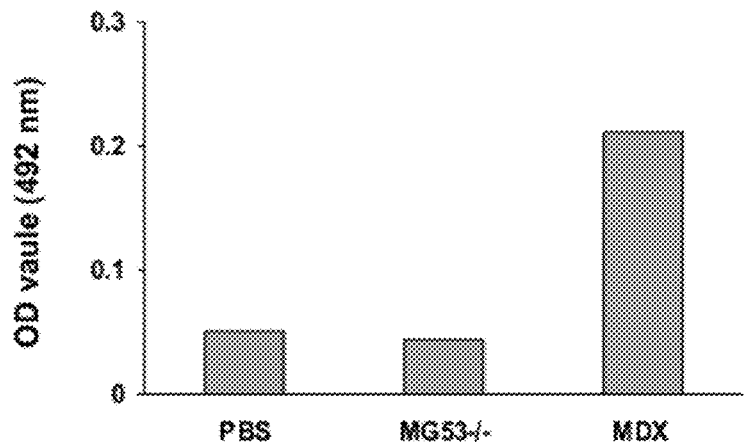

SEQUENCE LISTING

<160> NUMBER OF SEQ ID NOS: 13

<210> SEQ ID NO 1
<211> LENGTH: 477
<212> TYPE: PRT
<213> ORGANISM: Homo sapiens
<220> FEATURE:
<221> NAME/KEY: misc_feature
<222> LOCATION: (1)..(477)
<223> OTHER INFORMATION: Human MG53 Polypeptide

<400> SEQUENCE: 1

```
Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Gly Arg Val Ala Gly Glu Pro Ala Ala Asp
        35                  40                  45

Gly Thr Val Leu Cys Pro Cys Cys Gln Ala Pro Thr Arg Pro Gln Ala
    50                  55                  60

Leu Ser Thr Asn Leu Gln Leu Ala Arg Leu Val Glu Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Ala Leu Val Cys Gly Val Cys Ala Ser Leu Gly
            100                 105                 110

Ser His Arg Gly His Arg Leu Leu Pro Ala Ala Glu Ala His Ala Arg
        115                 120                 125

Leu Lys Thr Gln Leu Pro Gln Gln Lys Leu Gln Leu Gln Glu Ala Cys
    130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Val Phe Leu Ala Ala Leu Glu Gly Ser Leu Asp Cys
            180                 185                 190

Glu Ala Glu Arg Val Arg Gly Glu Ala Gly Val Ala Leu Arg Arg Glu
        195                 200                 205

Leu Gly Ser Leu Asn Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
                245                 250                 255

Pro Pro Ala Arg Leu Asp Ile Gln Leu Pro Ile Ile Ser Asp Asp Phe
            260                 265                 270

Lys Phe Gln Val Trp Arg Lys Met Phe Arg Ala Leu Met Pro Ala Leu
        275                 280                 285

Glu Glu Leu Thr Phe Asp Pro Ser Ser Ala His Pro Ser Leu Val Val
    290                 295                 300

Ser Ser Ser Gly Arg Arg Val Glu Cys Ser Glu Gln Lys Ala Pro Pro
305                 310                 315                 320

Ala Gly Glu Asp Pro Arg Gln Phe Asp Lys Ala Val Ala Val Val Ala
                325                 330                 335

His Gln Gln Leu Ser Glu Gly Glu His Tyr Trp Glu Val Asp Val Gly
```

```
                340             345             350
Asp Lys Pro Arg Trp Ala Leu Gly Val Ile Ala Glu Ala Pro Arg
            355                 360                 365

Arg Gly Arg Leu His Ala Val Pro Ser Gln Gly Leu Trp Leu Gly
        370                 375                 380

Leu Arg Glu Gly Lys Ile Leu Glu Ala His Val Glu Ala Lys Glu Pro
385                 390                 395                 400

Arg Ala Leu Arg Ser Pro Glu Arg Pro Thr Arg Ile Gly Leu Tyr
                405                 410                 415

Leu Ser Phe Gly Asp Gly Val Leu Ser Phe Tyr Asp Ala Ser Asp Ala
                    420                 425                 430

Asp Ala Leu Val Pro Leu Phe Ala Phe His Glu Arg Leu Pro Arg Pro
                435                 440                 445

Val Tyr Pro Phe Phe Asp Val Cys Trp His Asp Lys Gly Lys Asn Ala
            450                 455                 460

Gln Pro Leu Leu Leu Val Gly Pro Glu Gly Ala Glu Ala
465                 470                 475

<210> SEQ ID NO 2
<211> LENGTH: 1434
<212> TYPE: DNA
<213> ORGANISM: Homo sapiens
<220> FEATURE:
<221> NAME/KEY: misc_feature
<222> LOCATION: (1)..(1434)
<223> OTHER INFORMATION: Human MG53 cDNA

<400> SEQUENCE: 2
atgtcggctg cgcccggcct cctgcaccag gagctgtcct gcccgctgtg cctgcagctg      60
ttcgacgcgc ccgtgacagc cgagtgcggc cacagtttct gccgcgcctg cctaggccgc     120
gtggccgggg agccggcggc ggatggcacc gttctctgcc cctgctgcca ggcccccacg     180
cggccgcagg cactcagcac caacctgcag ctggcgcgcc tggtggaggg gctggcccag     240
gtgccgcagg ccactgcgcg ggagcacctg gacccgctga gcatctactg cgagcaggac     300
cgcgcgctgg tgtgcggagt gtgcgcctca ctcggctcgc accgcggtca tcgcctcctg     360
cctgccgccg aggcccacgc acgcctcaag acacagctgc acagcagaaa actgcagctg     420
caggaggcat gcatgcgtaa ggagaagagt gtggctgtgc tggagcatca gctggtggag     480
gtggaggaga cagtgcgtca gttccggggg gccgtggggg agcagctggg caagatgcgg     540
gtgttcctgg ctgcactgga gggctccttg gactgcgagg cagagcgtgt acggggtgag     600
gcaggggtcg ccttgcgccg ggagctgggg agcctgaact cttacctgga gcagctgcgg     660
cagatggaga aggtcctgga ggaggtggcg gacaagccgc agactgagtt cctcatgaaa     720
tactgcctgg tgaccagcag gctgcagaag atcctggcag agtctccccc acccgcccgt     780
ctggacatcc agctgccaat tatctcagat gacttcaaat tccaggtgtg gaggaagatg     840
ttccgggctc tgatgccagc gctggaggag ctgacctttg acccgagctc tgcgcacccg     900
agcctggtgg tgtcttcctc tggccgccgc gtggagtgct cggagcagaa ggcgccgccg     960
gccggggagg acccgcgcca gttcgacaag gcggtggcgg tggtggcgca ccagcagctc    1020
tccgagggcg agcactactg ggaggtggat gttggcgaca gccgcgctg ggcgctgggc    1080 gtgatcgcgg ccgaggcccc ccgccgcggg cgcctgcacg cggtgccctc gcagggcctg    1140
tggctgctgg ggctgcgcga gggcaagatc ctggaggcac acgtggaggc caaggagccg    1200
cgcgctctgc gcagccccga gaggcggccc acgcgcattg gcctttacct gagcttcggc    1260
```

-continued

```
gacggcgtcc tctccttcta cgatgccagc gacgccgacg cgctcgtgcc gcttttttgcc    1320 ttccacgagc gcctgcccag gcccgtgtac cccttcttcg acgtgtgctg cacgacaag     1380 ggcaagaatg cccagccgct gctgctcgtg ggtcccgaag cgccgaggc ctga            1434
```

<210> SEQ ID NO 3
<211> LENGTH: 477
<212> TYPE: PRT
<213> ORGANISM: Mus musculus
<220> FEATURE:
<221> NAME/KEY: misc_feature
<222> LOCATION: (1)..(477)
<223> OTHER INFORMATION: Mouse MG53

<400> SEQUENCE: 3

```
Met Ser Ala Ala Pro Gly Leu Leu Arg Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Ile Arg Val Ala Gly Glu Pro Ala Ala Asp
        35                  40                  45

Gly Thr Val Ala Cys Pro Cys Cys Gln Ala Pro Thr Arg Pro Gln Ala
    50                  55                  60

Leu Ser Thr Asn Leu Gln Leu Ser Arg Leu Val Glu Gly Leu Ala Gln
65                  70                  75                  80

Val Pro Gln Gly His Cys Glu His Leu Asp Pro Leu Ser Ile Tyr
                85                  90                  95

Cys Glu Gln Asp Arg Thr Leu Val Cys Gly Val Cys Ala Ser Leu Gly
            100                 105                 110

Ser His Arg Gly His Arg Leu Leu Pro Ala Ala Glu Ala Gln Ala Arg
        115                 120                 125

Leu Lys Thr Gln Leu Pro Gln Gln Lys Met Gln Leu Gln Glu Ala Cys
    130                 135                 140

Met Arg Lys Glu Lys Thr Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Met Phe Leu Ala Ala Leu Glu Ser Ser Leu Asp Arg
            180                 185                 190

Glu Ala Glu Arg Val Arg Gly Asp Ala Gly Val Ala Leu Arg Arg Glu
        195                 200                 205

Leu Ser Ser Leu Asn Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Phe Cys Leu Val Thr Ser Arg Leu Gln Lys Ile Leu Ser Glu Ser Pro
                245                 250                 255

Pro Pro Ala Arg Leu Asp Ile Gln Leu Pro Val Ile Ser Asp Asp Phe
            260                 265                 270

Lys Phe Gln Val Trp Lys Lys Met Phe Arg Ala Leu Met Pro Ala Leu
        275                 280                 285

Glu Glu Leu Thr Phe Asp Pro Ser Ser Ala His Pro Ser Leu Val Val
    290                 295                 300

Ser Ser Ser Gly Arg Arg Val Glu Cys Ser Asp Gln Lys Ala Pro Pro
305                 310                 315                 320

Ala Gly Glu Asp Thr Arg Gln Phe Asp Lys Ala Val Ala Val Val Ala
                325                 330                 335
```

```
Gln Gln Leu Leu Ser Gln Gly Glu His Tyr Trp Glu Val Glu Val Gly
        340                 345                 350
Asp Lys Pro Arg Trp Ala Leu Gly Val Met Ala Ala Asp Ala Ser Arg
        355                 360                 365
Arg Gly Arg Leu His Ala Val Pro Ser Gln Gly Leu Trp Leu Leu Gly
        370                 375                 380
Leu Arg Asp Gly Lys Ile Leu Glu Ala His Val Glu Ala Lys Glu Pro
385                 390                 395                 400
Arg Ala Leu Arg Thr Pro Glu Arg Pro Pro Ala Arg Ile Gly Leu Tyr
                405                 410                 415
Leu Ser Phe Ala Asp Gly Val Leu Ala Phe Tyr Asp Ala Ser Asn Pro
            420                 425                 430
Asp Val Leu Thr Pro Ile Phe Ser Phe His Glu Arg Leu Pro Gly Pro
                435                 440                 445
Val Tyr Pro Ile Phe Asp Val Cys Trp His Asp Lys Gly Lys Asn Ala
        450                 455                 460
Gln Pro Leu Leu Leu Val Gly Pro Glu Gln Glu Gln Ala
465                 470                 475

<210> SEQ ID NO 4
<211> LENGTH: 1434
<212> TYPE: DNA
<213> ORGANISM: Mus musculus
<220> FEATURE:
<221> NAME/KEY: misc_feature
<222> LOCATION: (1)..(1434)
<223> OTHER INFORMATION: Mouse MG53 cDNA

<400> SEQUENCE: 4
atgtcggctg cacccggcct tctgcgtcag gaactgtcct gcccactgtg cttgcagctg      60
ttcgatgcgc cagtgacggc tgagtgtggc cacagtttct gccgtgcctg cctgatccgg     120
gtggcagggg agcctgctgc ggacggcaca gttgcctgtc cctgttgtca ggcacctaca     180
cggccgcagg ctctaagcac taacctccag ttgtcacgcc ttgtggaggg tttggcgcaa     240
gtgccccaag ccactgcgga ggaacacctg gatccactga gcatctactg cgagcaggac     300
cgcacacttg tgtgtggtgt gtgtgcctcg ctcggttctc accgtggtca tcgtctcctg     360
cctgccgctg aagcccaagc acgcctcaag acacagcttc cacagcagaa gatgcagctg     420
caggaggcat gcatgcgcaa ggagaagact gtagcggtgc tggagcatca gctggtggag     480
gtggaggaga cagtgcgcca gttccgggga gctgtcgggg agcagctggg gaagatgcgg     540
atgttcctgg ctgccctaga aagttctctg gaccgtgaag cagaaagggt tcggggtgat     600 gctgggggttg ccttgcgtcg ggagctgtca agcctgaact cttacctaga gcaactgagg     660
cagatggaga aggtgctgga ggaggtggct gacaagccac agacagaatt cctcatgaaa     720
ttctgcctgg taaccagcag gctgcagaag atcctgtcag agtcaccacc accggcaagg     780
ctagatatcc agctgcctgt catctcagat gacttcaaat tccaggtgtg aagaagatg      840 ttccgggctc tgatgccagc gctggaggaa ctgactttttg accccagctc tgcgcacccg     900
agcctggtgg tgtcctcctc tggtcgccga gtggagtgct cagaccagaa ggcgccgcca     960
gcgggagaag acacgcgtca gttcgacaag gcagtagcgg tggtggcgca gcagctgctg    1020
tcacagggcg agcactattg ggaggtggag gtgggcgaca accacgctg gcccctggga     1080 gtgatggcgg ctgacgcttc ccgccgtggc cggctgcacg cggtgccctc acaggggctg    1140
tggctgctgg gtctgcgcga tggcaagatc ctggaggcgc acgtggaggc caaggagccg    1200
```

```
cgggcactgc gcaccccaga gaggcctccg gcgcgcattg gcctctacct aagcttcgca  1260
gatggcgtcc tggctttcta tgatgcgagc aaccccgacg tacttacgcc aatctttttct  1320 ttccacgagc gtctgcccgg gccggtgtac cccatctttg acgtgtgctg gcacgacaag  1380
ggcaagaatg cccagcccct gctgcttgtg gggccggagc aggaacaggc ctga         1434
```

<210> SEQ ID NO 5
<211> LENGTH: 477
<212> TYPE: PRT
<213> ORGANISM: Oryctolagus cuniculus
<220> FEATURE:
<221> NAME/KEY: misc_feature
<222> LOCATION: (1)..(477)
<223> OTHER INFORMATION: Rabbit MG53

<400> SEQUENCE: 5

```
Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Ser Arg Val Ala Gly Glu Pro Ala Ala Asp
        35                  40                  45

Gly Thr Val Asn Cys Pro Cys Cys Gln Ala Pro Thr Arg Pro Gln Ala
    50                  55                  60

Leu Ser Thr Asn Leu Gln Leu Ala Arg Leu Val Glu Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Val Leu Val Cys Gly Val Cys Ala Ser Leu Gly
            100                 105                 110

Ser His Arg Gly His Arg Leu Leu Pro Ala Ala Glu Ala His Ser Arg
        115                 120                 125

Leu Lys Thr Gln Leu Pro Gln Gln Lys Leu Gln Leu Gln Glu Ala Ser
    130                 135                 140

Met Arg Lys Glu Lys Ser Val Ala Val Leu Glu His Gln Leu Thr Glu
145                 150                 155                 160

Val Glu Glu Thr Val Arg Gln Phe Arg Gly Ala Val Gly Glu Gln Leu
                165                 170                 175

Gly Lys Met Arg Val Phe Leu Ala Ala Leu Glu Gly Ser Leu Asp Arg
            180                 185                 190

Glu Ala Glu Arg Val Arg Ser Glu Ala Gly Val Ala Leu Arg Arg Glu
        195                 200                 205

Leu Gly Gly Leu His Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
                245                 250                 255

Pro Pro Ala Arg Leu Asp Ile Gln Leu Pro Ile Ile Ser Asp Asp Phe
            260                 265                 270

Lys Phe Gln Val Trp Arg Lys Met Phe Arg Ala Leu Met Pro Ala Leu
        275                 280                 285

Glu Glu Leu Thr Phe Asp Pro Ser Ser Ala His Pro Ser Leu Val Val
    290                 295                 300

Ser Pro Thr Gly Arg Arg Val Glu Cys Ser Glu Gln Lys Ala Pro Pro
305                 310                 315                 320
```

```
Ala Gly Asp Asp Ala Arg Gln Phe Asp Lys Ala Val Ala Val Val Ala
            325                 330                 335

Gln Gln Leu Leu Ser Asp Gly Glu His Tyr Trp Glu Val Glu Val Gly
        340                 345                 350

Asp Lys Pro Arg Trp Ala Leu Gly Val Met Ala Ser Glu Ala Ser Arg
    355                 360                 365

Arg Gly Arg Leu His Ala Val Pro Ser Gln Gly Leu Trp Leu Leu Gly
370                 375                 380

Leu Arg Asp Gly Lys Thr Leu Glu Ala His Val Gly Ala Lys Glu Pro
385                 390                 395                 400

Arg Ala Leu Arg Thr Pro Glu Arg Pro Thr Arg Leu Gly Leu Tyr
            405                 410                 415

Leu Ser Phe Gly Asp Gly Val Leu Ala Phe Tyr Asp Ala Ser Asp Ala
        420                 425                 430

Asp Ala Leu Glu Leu Leu Phe Ala Phe Arg Glu Arg Leu Pro Gly Pro
    435                 440                 445

Val Tyr Pro Phe Phe Asp Val Cys Trp His Asp Lys Gly Lys Asn Ala
450                 455                 460

Gln Pro Leu Leu Leu Val Gly Pro Asp Gly Gln Glu Ala
465                 470                 475

<210> SEQ ID NO 6
<211> LENGTH: 477
<212> TYPE: PRT
<213> ORGANISM: Canis sp.
<220> FEATURE:
<221> NAME/KEY: MISC_FEATURE
<222> LOCATION: (1)..(477)

<400> SEQUENCE: 6

Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Ser Arg Val Ala Gly Glu Pro Ala Ala Asp
        35                  40                  45

Gly Thr Val Pro Cys Pro Cys Cys Gln Ala Leu Thr Arg Pro Gln Ala
    50                  55                  60

Leu Ser Thr Asn Gln Gln Leu Ala Arg Leu Val Glu Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Ala Leu Val Cys Gly Val Cys Ala Ser Leu Gly
            100                 105                 110

Ser His Arg Gly His Arg Leu Leu Pro Ala Ala Glu Ala His Ala Arg
        115                 120                 125

Leu Lys Thr Gln Leu Pro Gln Gln Lys Leu Gln Leu Gln Glu Ala Cys
    130                 135                 140

Met Arg Lys Glu Lys Ser Val Ala Leu Leu Glu His Gln Leu Met Glu
145                 150                 155                 160

Val Glu Glu Met Val Arg Gln Phe Arg Gly Ala Val Gly Glu Gln Leu
                165                 170                 175

Gly Lys Met Arg Val Phe Leu Ala Ala Leu Glu Gly Ser Leu Asp Arg
            180                 185                 190

Glu Ala Glu Arg Val Arg Gly Glu Ala Gly Val Ala Leu Arg Arg Glu
        195                 200                 205
```

```
Leu Gly Ser Leu Asn Ser Tyr Leu Glu Gln Leu Arg Gln Met Glu Lys
    210                 215                 220
Val Leu Glu Glu Val Ala Asp Lys Pro Gln Thr Glu Phe Leu Met Lys
225                 230                 235                 240
Tyr Cys Leu Val Thr Ser Arg Leu Gln Lys Ile Leu Ala Glu Ser Pro
                245                 250                 255
Pro Pro Ala Arg Leu Asp Ile Gln Leu Pro Val Ile Ser Asp Asp Phe
            260                 265                 270
Lys Phe Gln Val Trp Arg Lys Met Phe Arg Ala Leu Met Pro Val Thr
        275                 280                 285
Lys Glu Leu Thr Phe Asp Pro Ser Ser Ala His Pro Ser Leu Val Leu
    290                 295                 300
Ser Pro Ser Gly Arg Arg Val Glu Cys Ser Asp Gln Lys Ala Pro Pro
305                 310                 315                 320
Ala Gly Glu Asp Pro Cys Gln Phe Asp Lys Ala Val Ala Val Val Ala
                325                 330                 335
Gln Gln Val Leu Ser Asp Gly Glu His Tyr Trp Glu Val Gln Val Gly
            340                 345                 350
Glu Lys Pro Arg Trp Ala Leu Gly Val Ile Ala Ala Gln Ala Ser Arg
        355                 360                 365
Arg Gly Arg Leu His Ala Val Pro Ser Gln Gly Leu Trp Leu Leu Gly
    370                 375                 380
Leu Arg Asp Gly Lys Ile Leu Glu Ala His Val Glu Ala Lys Glu Pro
385                 390                 395                 400
Arg Ala Leu Arg Thr Pro Glu Arg Arg Pro Thr Arg Ile Gly Ile Tyr
                405                 410                 415
Leu Ser Phe Gly Asp Gly Val Leu Ser Phe Tyr Asp Ala Ser Asp Pro
            420                 425                 430
Asp Ala Leu Glu Leu Leu Phe Ala Phe His Glu Arg Leu Pro Gly Pro
        435                 440                 445
Val Tyr Pro Phe Phe Asp Val Cys Trp His Asp Lys Gly Lys Asn Ala
    450                 455                 460
Gln Pro Leu Leu Leu Val Gly Pro Asp Gly Glu Glu Ala
465                 470                 475

<210> SEQ ID NO 7
<211> LENGTH: 477
<212> TYPE: PRT
<213> ORGANISM: Pan troglodytes
<220> FEATURE:
<221> NAME/KEY: MISC_FEATURE
<222> LOCATION: (1)..(477)

<400> SEQUENCE: 7

Met Ser Ala Ala Pro Gly Leu Leu His Gln Glu Leu Ser Cys Pro Leu
1               5                   10                  15
Cys Leu Gln Leu Phe Asp Ala Pro Val Thr Ala Glu Cys Gly His Ser
            20                  25                  30
Phe Cys Arg Ala Cys Leu Gly Arg Val Ala Gly Glu Pro Ala Ala Asp
        35                  40                  45
Gly Thr Val Leu Cys Pro Cys Gln Ala Pro Thr Arg Pro Gln Ala
    50                  55                  60
Leu Ser Thr Asn Leu Gln Leu Ala Arg Leu Val Glu Gly Leu Ala Gln
65                  70                  75                  80
Val Pro Gln Gly His Cys Glu Glu His Leu Asp Pro Leu Ser Ile Tyr
                85                  90                  95
```

-continued

Cys Glu Gln Asp Arg Ala Leu Val Cys Gly Val Cys Ala Ser Leu Gly
                100                 105                 110

Ser His Arg Gly His Arg Leu Leu Pro Ala Ala Glu Ala His Ala Arg
            115                 120                 125

Leu Lys Thr Gln Leu Pro Gln Gln Lys Leu Gln Leu Gln Glu Ala Cys
        130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Val Phe Leu Ala Ala Leu Glu Gly Ser Leu Asp Arg
            180                 185                 190

Glu Ala Glu Arg Val Arg Gly Glu Ala Gly Val Ala Leu Arg Arg Glu
        195                 200                 205

Leu Gly Ser Leu Asn Ser Tyr Leu Glu Gln Leu Arg Gln Met Glu Lys
210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
                245                 250                 255

Pro Pro Ala Arg Leu Asp Ile Gln Leu Pro Ile Ile Ser Asp Asp Phe
            260                 265                 270

Lys Phe Gln Val Trp Arg Lys Met Phe Arg Ala Leu Met Pro Ala Leu
        275                 280                 285

Glu Glu Leu Thr Phe Asp Pro Ser Ser Ala His Pro Ser Leu Val Val
290                 295                 300

Ser Ser Ser Gly Arg Arg Val Glu Cys Ser Glu Gln Lys Ala Pro Pro
305                 310                 315                 320

Ala Gly Glu Asp Pro Arg Gln Phe Asp Lys Ala Val Ala Val Val Ala
                325                 330                 335

His Gln Gln Leu Ser Glu Gly Glu His Tyr Trp Glu Val Asp Val Gly
            340                 345                 350

Asp Lys Pro Arg Trp Ala Leu Gly Val Ile Ala Ala Glu Ala Pro Arg
        355                 360                 365

Arg Gly Arg Leu His Ala Val Pro Ser Gln Gly Leu Trp Leu Leu Gly
370                 375                 380

Leu Arg Glu Gly Lys Ile Leu Glu Ala His Val Glu Ala Lys Glu Pro
385                 390                 395                 400

Arg Ala Leu Arg Ser Pro Glu Arg Arg Pro Thr Arg Ile Gly Leu Tyr
                405                 410                 415

Leu Ser Phe Gly Asp Gly Val Leu Ser Phe Tyr Asp Ala Ser Asp Ala
            420                 425                 430

Asp Ala Leu Val Pro Leu Phe Ala Phe His Glu Arg Leu Pro Arg Pro
        435                 440                 445

Val Tyr Pro Phe Phe Asp Val Cys Trp His Asp Lys Gly Lys Asn Ala
        450                 455                 460

Gln Pro Leu Leu Leu Val Gly Pro Glu Gly Ala Glu Ala
465                 470                 475

<210> SEQ ID NO 8
<211> LENGTH: 477
<212> TYPE: PRT
<213> ORGANISM: Macaca mulatta
<220> FEATURE:
<221> NAME/KEY: MISC_FEATURE
<222> LOCATION: (1)..(477)

```
<400> SEQUENCE: 8

Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Gly Arg Val Ala Gly Glu Pro Ala Ala Asp
        35                  40                  45

Gly Thr Val Leu Cys Pro Cys Cys Gln Ala Pro Thr Arg Pro Gln Ala
    50                  55                  60

Leu Ser Thr Asn Leu Gln Leu Ala Arg Leu Val Glu Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Ala Leu Val Cys Gly Val Cys Ala Ser Leu Gly
            100                 105                 110

Ser His Arg Gly His Arg Leu Leu Pro Ala Ala Glu Ala His Ala Arg
        115                 120                 125

Leu Lys Thr Gln Leu Pro Gln Gln Lys Leu Gln Leu Gln Glu Ala Cys
    130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Val Phe Leu Ala Ala Leu Glu Gly Ser Leu Asp Arg
            180                 185                 190

Glu Ala Glu Arg Val Arg Gly Glu Ala Gly Val Ala Leu Arg Arg Glu
        195                 200                 205

Leu Gly Ser Leu Asn Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
                245                 250                 255

Pro Pro Ala Arg Leu Asp Ile Gln Leu Pro Ile Ile Ser Asp Asp Phe
            260                 265                 270

Lys Phe Gln Val Trp Arg Lys Met Phe Arg Ala Leu Met Pro Ala Leu
        275                 280                 285

Glu Glu Leu Thr Phe Asp Pro Ser Ser Ala His Pro Ser Leu Val Val
    290                 295                 300

Ser Ser Ser Gly Arg Arg Val Glu Cys Ser Glu Gln Lys Ala Pro Pro
305                 310                 315                 320

Ala Gly Glu Asp Pro Arg Gln Phe Asp Lys Ala Val Ala Val Ala
                325                 330                 335

His Gln Gln Leu Ser Glu Gly Glu His Tyr Trp Glu Val Glu Val Gly
            340                 345                 350

Asp Lys Pro Arg Trp Ala Leu Gly Val Ile Ala Ala Glu Gly Pro Arg
        355                 360                 365

Arg Gly Arg Leu His Ala Val Pro Ser Gln Gly Leu Trp Leu Leu Gly
    370                 375                 380

Leu Arg Glu Gly Lys Ile Leu Glu Ala His Val Glu Ala Lys Glu Pro
385                 390                 395                 400

Arg Ala Leu Arg Ser Pro Glu Arg Pro Thr Arg Ile Gly Leu Tyr
                405                 410                 415
```

```
Leu Ser Phe Gly Asp Gly Val Leu Ser Phe Tyr Asp Ala Ser Asp Ala
            420                 425                 430

Asp Ala Leu Val Pro Leu Phe Ala Phe His Glu Arg Leu Pro Gly Pro
            435                 440                 445

Val Tyr Pro Phe Phe Asp Val Cys Trp His Asp Lys Gly Lys Asn Ser
450                 455                 460

Gln Pro Leu Leu Leu Val Gly Ser Glu Gly Ala Glu Ala
465                 470                 475

<210> SEQ ID NO 9
<211> LENGTH: 482
<212> TYPE: PRT
<213> ORGANISM: Bos sp.
<220> FEATURE:
<221> NAME/KEY: 'MISC_FEATURE
<222> LOCATION: (1)..(482)

<400> SEQUENCE: 9

Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Ser Arg Val Ala Gly Glu Pro Ala Ala Asp
        35                  40                  45

Gly Thr Val Leu Cys Pro Ser Cys Gln Ala Pro Thr Arg Pro Gln Ala
    50                  55                  60

Leu Ser Thr Asn Leu Gln Leu Ala Arg Leu Val Glu Gly Leu Ala Gln
65                  70                  75                  80

Val Pro Gln Gly His Cys Glu Glu His Leu Asp Pro Leu Ser Ile Tyr
            85                  90                  95

Cys Glu Gln Asp Arg Ala Leu Val Cys Gly Val Cys Ala Ser Leu Gly
        100                 105                 110

Ser His Arg Gly His Arg Leu Leu Pro Ala Ala Glu Ala His Ala Arg
    115                 120                 125

Leu Lys Thr Gln Leu Pro Gln Gln Lys Met Gln Leu Gln Glu Ala Cys
130                 135                 140

Met Arg Lys Glu Lys Ser Val Ala Leu Leu Glu His Gln Leu Leu Glu
145                 150                 155                 160

Val Glu Glu Thr Val Arg Gln Phe Arg Gly Ala Val Gly Glu Gln Leu
            165                 170                 175

Gly Lys Met Arg Leu Phe Leu Ala Ala Leu Glu Gly Ser Leu Asp Arg
        180                 185                 190

Glu Ala Glu Arg Val Arg Gly Glu Ala Gly Val Ala Leu Arg Arg Glu
    195                 200                 205

Leu Gly Ser Leu Asn Ser Tyr Leu Glu Gln Leu Arg Gln Met Glu Lys
210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
            245                 250                 255

Pro Pro Ala Arg Leu Asp Ile Gln Leu Pro Ile Ile Ser Asp Asp Phe
        260                 265                 270

Lys Phe Gln Val Trp Arg Lys Met Phe Arg Ala Leu Met Pro Ala Arg
    275                 280                 285

Gln Glu Leu Thr Phe Asp Pro Ser Thr Ala His Pro Ser Leu Val Leu
290                 295                 300
```

```
Ser Asn Ser Gly Arg Cys Val Glu Cys Ser Glu Gln Lys Ala Pro Pro
305                 310                 315                 320

Ala Gly Glu Asp Pro Arg Gln Phe Asp Lys Ala Val Ala Val Val Thr
                325                 330                 335

His Gln Leu Leu Ser Glu Gly Glu His Tyr Trp Glu Val Val Val Gly
            340                 345                 350

Asp Lys Pro Arg Trp Ala Leu Gly Val Ile Gly Ala Gln Ala Gly Arg
        355                 360                 365

Arg Gly Arg Leu His Ala Val Pro Ser Gln Gly Leu Trp Leu Leu Gly
    370                 375                 380

Leu Arg Asp Gly Lys Ile Leu Glu Ala His Val Glu Ala Lys Glu Pro
385                 390                 395                 400

Arg Ala Leu Arg Thr Pro Glu Arg Arg Pro Thr Arg Ile Gly Ile Tyr
                405                 410                 415

Leu Ser Phe Gly Asp Gly Val Leu Ser Phe Tyr Asp Ala Ser Asp Pro
            420                 425                 430

Asp Ala Leu Glu Leu Leu Phe Ala Phe His Glu Arg Leu Pro Gly Pro
        435                 440                 445

Val Tyr Pro Phe Phe Asp Val Cys Trp His Asp Lys Gly Lys Asn Ala
    450                 455                 460

Gln Pro Leu Leu Val Gly Pro Glu Val Ser Gly Gly Ser Gly Ser
465                 470                 475                 480

Glu Ala

<210> SEQ ID NO 10
<211> LENGTH: 477
<212> TYPE: PRT
<213> ORGANISM: Rattus sp.
<220> FEATURE:
<221> NAME/KEY: MISC_FEATURE
<222> LOCATION: (1)..(477)

<400> SEQUENCE: 10

Met Ser Thr Ala Pro Gly Leu Leu Arg Gln Glu Leu Ser Cys Pro Leu
1               5                   10                  15

Cys Leu Gln Leu Phe Asp Ala Pro Val Thr Ala Glu Cys Gly His Ser
                20                  25                  30

Phe Cys Arg Ala Cys Leu Ile Arg Val Ala Gly Glu Pro Ala Asp Asp
            35                  40                  45

Gly Thr Val Ala Cys Pro Cys Cys Gln Ala Ser Thr Arg Pro Gln Ala
        50                  55                  60

Leu Ser Thr Asn Leu Gln Leu Ala Arg Leu Val Glu Gly Leu Ala Gln
65                  70                  75                  80

Val Pro Gln Gly His Cys Glu His Leu Asp Pro Leu Ser Ile Tyr
                85                  90                  95

Cys Glu Gln Asp Arg Thr Leu Val Cys Gly Val Cys Ala Ser Leu Gly
                100                 105                 110

Ser His Arg Gly His Arg Leu Leu Pro Ala Ala Glu Ala His Ala Arg
            115                 120                 125

Leu Lys Thr Gln Leu Pro Gln Gln Lys Ala Gln Leu Gln Glu Ala Cys
        130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175
```

```
Gly Lys Met Arg Met Phe Leu Ala Ala Leu Glu Ser Ser Leu Asp Arg
            180                 185                 190

Glu Ala Glu Arg Val Arg Gly Glu Ala Gly Val Ala Leu Arg Arg Glu
                195                 200                 205

Leu Ser Ser Leu Asn Ser Tyr Leu Glu Gln Leu Arg Gln Met Glu Lys
210                 215                 220

Val Leu Glu Glu Val Ala Asp Lys Pro Gln Thr Glu Phe Leu Met Lys
225                 230                 235                 240

Phe Cys Leu Val Thr Ser Arg Leu Gln Lys Ile Leu Ser Glu Ser Pro
                245                 250                 255

Pro Pro Ala Arg Leu Asp Ile Gln Leu Pro Val Ile Ser Asp Asp Phe
                260                 265                 270

Lys Phe Gln Val Trp Lys Lys Met Phe Arg Ala Leu Met Pro Glu Leu
            275                 280                 285

Glu Glu Leu Thr Phe Asp Pro Ser Ala His Pro Ser Leu Val Val
290                 295                 300

Ser Ala Ser Gly Arg Arg Val Glu Cys Ser Glu Gln Lys Ala Pro Pro
305                 310                 315                 320

Ala Gly Glu Asp Thr Cys Gln Phe Asp Lys Thr Val Ala Val Ala
                325                 330                 335

Lys Gln Leu Leu Ser Gln Gly Glu His Tyr Trp Glu Val Glu Val Gly
            340                 345                 350

Asp Lys Pro Arg Trp Ala Leu Gly Val Met Ala Ala Asp Ala Ser Arg
                355                 360                 365

Arg Gly Arg Leu His Ala Val Pro Ser Gln Gly Leu Trp Leu Leu Gly
370                 375                 380

Leu Arg Asp Gly Lys Ile Leu Glu Ala His Val Glu Ala Lys Glu Pro
385                 390                 395                 400

Arg Ala Leu Arg Thr Pro Glu Arg Pro Pro Ala Arg Ile Gly Leu Tyr
                405                 410                 415

Leu Ser Phe Ala Asp Gly Val Leu Thr Phe Tyr Asp Ala Ser Asn Thr
                420                 425                 430

Asp Ala Leu Thr Pro Leu Phe Ser Phe His Glu Arg Leu Pro Gly Pro
                435                 440                 445

Val Tyr Pro Met Phe Asp Val Cys Trp His Asp Lys Gly Lys Asn Ser
450                 455                 460

Gln Pro Leu Leu Leu Val Gly Pro Asp Ser Glu Gln Ala
465                 470                 475

<210> SEQ ID NO 11
<211> LENGTH: 477
<212> TYPE: PRT
<213> ORGANISM: Xenopus laevis
<220> FEATURE:
<221> NAME/KEY: MISC_FEATURE
<222> LOCATION: (1)..(477)

<400> SEQUENCE: 11

Met Ser Thr Pro Gln Leu Met Gln Gly Met Gln Lys Asp Leu Thr Cys
1               5                   10                  15

Gln Leu Cys Leu Glu Leu Phe Arg Ala Pro Val Thr Pro Glu Cys Gly
                20                  25                  30

His Thr Phe Cys Gln Gly Cys Leu Thr Gly Val Pro Lys Asn Gln Asp
            35                  40                  45

Gln Asn Gly Ser Thr Pro Cys Pro Thr Cys Gln Ser Pro Ser Arg Pro
        50                  55                  60
```

-continued

```
Glu Thr Leu Gln Ile Asn Arg Gln Leu Glu His Leu Val Gln Ser Phe
 65                  70                  75                  80

Lys Gln Val Pro Gln Gly His Cys Leu Glu His Met Asp Pro Leu Ser
                 85                  90                  95

Val Tyr Cys Glu Gln Asp Lys Glu Leu Ile Cys Gly Val Cys Ala Ser
            100                 105                 110

Leu Gly Lys His Lys Gly His Asn Ile Ile Thr Ala Ser Glu Ala Phe
        115                 120                 125

Ala Lys Leu Lys Arg Gln Leu Pro Gln Gln Val Ile Leu Gln Glu
130                 135                 140

Ala Arg Leu Lys Lys Glu Lys Thr Val Ala Val Leu Asp Arg Gln Val
145                 150                 155                 160

Ala Glu Val Gln Asp Thr Val Ser Arg Phe Lys Gly Asn Val Lys His
                165                 170                 175

Gln Leu Asn Ala Met Arg Ser Tyr Leu Asn Ile Met Glu Ala Ser Leu
            180                 185                 190

Gly Lys Glu Ala Asp Lys Ala Glu Ser Ala Ala Thr Glu Ala Leu Leu
        195                 200                 205

Val Glu Arg Lys Thr Met Gly His Tyr Leu Asp Gln Leu Arg Gln Met
210                 215                 220

Glu Gly Val Leu Lys Asp Val Glu Gly Gln Glu Gln Thr Glu Phe Leu
225                 230                 235                 240

Arg Lys Tyr Cys Val Val Ala Ala Arg Leu Asn Lys Ile Leu Ser Glu
                245                 250                 255

Ser Pro Pro Gly Arg Leu Asp Ile Gln Leu Pro Ile Ile Ser Asp
            260                 265                 270

Glu Phe Lys Phe Gln Val Trp Arg Lys Met Phe Arg Ala Leu Met Pro
        275                 280                 285

Ala Leu Glu Asn Met Thr Phe Asp Pro Asp Thr Ala Gln Gln Tyr Leu
290                 295                 300

Val Val Ser Ser Glu Gly Lys Ser Val Glu Cys Ala Asp Gln Lys Gln
305                 310                 315                 320

Ser Val Ser Asp Glu Pro Asn Arg Phe Asp Lys Ser Asn Cys Leu Val
                325                 330                 335

Ser Lys Gln Ser Phe Thr Glu Gly His Tyr Trp Glu Val Ile Val
            340                 345                 350

Glu Asp Lys Pro Arg Trp Ala Leu Gly Ile Ile Ser Glu Thr Ala Asn
        355                 360                 365

Arg Lys Gly Lys Leu His Ala Thr Pro Ser Asn Gly Phe Trp Ile Ile
370                 375                 380

Gly Cys Lys Glu Gly Lys Val Tyr Glu Ala His Thr Glu Gln Lys Glu
385                 390                 395                 400

Pro Arg Val Leu Arg Val Glu Gly Arg Pro Glu Lys Ile Gly Val Tyr
                405                 410                 415

Leu Ser Phe Ser Asp Gly Val Val Ser Phe Asp Ser Ser Asp Glu
            420                 425                 430

Asp Asn Leu Lys Leu Leu Tyr Thr Phe Asn Glu Arg Phe Ser Gly Arg
        435                 440                 445

Leu His Pro Phe Phe Asp Val Cys Trp His Asp Lys Gly Lys Asn Ser
450                 455                 460

Gln Pro Leu Lys Ile Phe Tyr Pro Pro Ala Glu Gln Leu
465                 470                 475

<210> SEQ ID NO 12
```

```
<211> LENGTH: 477
<212> TYPE: PRT
<213> ORGANISM: Xenopus sp.
<220> FEATURE:
<221> NAME/KEY: MISC_FEATURE
<222> LOCATION: (1)..(477)

<400> SEQUENCE: 12
```

| Met<br>1 | Ser | Thr | Pro | Gln<br>5 | Leu | Met | Gln | Gly | Met<br>10 | Gln | Lys | Asp | Leu | Thr<br>15 | Cys |
|---|---|---|---|---|---|---|---|---|---|---|---|---|---|---|---|
| Pro | Leu | Cys | Leu<br>20 | Glu | Leu | Phe | Arg | Ala<br>25 | Pro | Val | Thr | Pro | Glu<br>30 | Cys | Gly |
| His | Thr | Phe<br>35 | Cys | Gln | Gly | Cys | Leu<br>40 | Thr | Gly | Ala | Pro | Lys<br>45 | Asn | Gln | Asp |
| Gln | Asn<br>50 | Gly | Ser | Thr | Pro | Cys<br>55 | Pro | Thr | Cys | Gln | Thr<br>60 | Pro | Ser | Arg | Pro |
| Glu<br>65 | Thr | Leu | Gln | Ile | Asn<br>70 | Arg | Gln | Leu | Glu | His<br>75 | Leu | Val | Gln | Ser | Phe<br>80 |
| Lys | Gln | Val | Pro | Lys<br>85 | Gly | His | Cys | Leu | Glu<br>90 | His | Leu | Asp | Pro | Leu<br>95 | Ser |
| Val | Tyr | Cys | Glu<br>100 | Gln | Asp | Lys | Glu | Leu<br>105 | Ile | Cys | Gly | Val | Cys<br>110 | Ala | Ser |
| Leu | Gly | Lys<br>115 | His | Lys | Gly | His | Asn<br>120 | Ile | Ile | Thr | Ala | Ala<br>125 | Glu | Ala | Tyr |
| Ala | Lys<br>130 | Leu | Lys | Arg | Gln | Leu<br>135 | Pro | Gln | Gln | Val | Ile<br>140 | Leu | Gln | Glu |  |
| Ala<br>145 | Arg | Leu | Lys | Lys | Glu<br>150 | Lys | Thr | Val | Ala | Val<br>155 | Leu | Asp | Arg | Gln | Val<br>160 |
| Ala | Glu | Val | Gln | Asp<br>165 | Thr | Val | Ser | Arg | Phe<br>170 | Lys | Gly | Asn | Val | Lys<br>175 | His |
| Gln | Leu | Asn | Ala<br>180 | Met | Arg | Ser | Tyr | Leu<br>185 | Ser | Ile | Met | Glu | Ala<br>190 | Ser | Leu |
| Ser | Lys<br>195 | Glu | Ala | Asp | Asn | Ala<br>200 | Glu | His | Thr | Ala | Thr<br>205 | Glu | Ala | Leu | Leu |
| Val | Glu<br>210 | Arg | Lys | Thr | Met | Gly<br>215 | His | Tyr | Leu | Asp | Gln<br>220 | Leu | Arg | Gln | Met |
| Asp<br>225 | Gly | Val | Leu | Lys | Asp<br>230 | Val | Glu | Ser | Gln | Glu<br>235 | Gln | Thr | Glu | Phe | Leu<br>240 |
| Arg | Lys | Tyr | Cys | Val<br>245 | Val | Ala | Ala | Arg | Leu<br>250 | Asn | Lys | Ile | Leu | Ala<br>255 | Glu |
| Ser | Pro | Pro | Gly<br>260 | Arg | Leu | Asp | Ile | Gln<br>265 | Leu | Pro | Ile | Ile | Ser<br>270 | Asp |  |
| Glu | Phe | Lys<br>275 | Phe | Gln | Val | Trp | Arg<br>280 | Lys | Met | Phe | Arg | Ala<br>285 | Leu | Met | Pro |
| Ala | Leu<br>290 | Glu | Asn | Leu | Thr | Phe<br>295 | Asp | Pro | Asp | Thr | Ala<br>300 | Gln | Gln | Asn | Leu |
| Val<br>305 | Val | Phe | Ser | Asp | Gly<br>310 | Lys | Ser | Val | Glu | Cys<br>315 | Ser | Glu | Gln | Lys | Gln<br>320 |
| Ser | Val | Ser | Asp | Glu<br>325 | Pro | Asn | Arg | Phe | Asp<br>330 | Lys | Ser | Asn | Cys | Leu<br>335 | Val |
| Ser | Lys | Glu | Ser<br>340 | Phe | Thr | Glu | Gly | Glu<br>345 | His | Tyr | Trp | Glu | Val<br>350 | Leu | Val |
| Glu | Asp | Lys<br>355 | Pro | Arg | Trp | Ala | Leu<br>360 | Gly | Val | Ile | Ser | Glu<br>365 | Thr | Ala | Asn |
| Arg | Lys<br>370 | Gly | Lys | Leu | His | Ala<br>375 | Ser | Pro | Ser | Asn | Gly<br>380 | Phe | Trp | Leu | Ile |

Gly Cys Lys Glu Gly Lys Val Tyr Glu Ala His Thr Glu Gln Lys Glu
385                 390                 395                 400

Pro Arg Val Leu Arg Val Gly Arg Pro Glu Lys Ile Gly Ile Tyr
            405                 410                 415

Leu Ser Phe Ser Asp Gly Val Val Ser Phe Asp Ser Asp Glu
            420                 425                 430

Asp Asn Ile Lys Leu Leu Tyr Thr Phe Asn Glu Arg Phe Ser Gly Arg
            435                 440                 445

Leu His Pro Phe Phe Asp Val Cys Trp His Lys Gly Lys Asn Ala
            450                 455                 460

Gln Pro Leu Lys Ile Phe Tyr Pro Pro Ala Glu Gln Leu
465                 470                 475

<210> SEQ ID NO 13
<211> LENGTH: 480
<212> TYPE: PRT
<213> ORGANISM: Artificial Sequence
<220> FEATURE:
<223> OTHER INFORMATION: Synthetic Sequence

<400> SEQUENCE: 13

Met Ser Ala Ala Pro Gly Leu Leu His Gly Met Gln Gln Glu Leu Ser
1               5                   10                  15

Cys Pro Leu Cys Leu Gln Leu Phe Asp Ala Pro Val Thr Ala Glu Cys
            20                  25                  30

Gly His Ser Phe Cys Arg Ala Cys Leu Arg Val Ala Gly Glu Pro Ala
        35                  40                  45

Ala Asp Gly Thr Val Leu Cys Pro Cys Cys Gln Ala Pro Thr Arg Pro
    50                  55                  60

Gln Ala Leu Ser Thr Asn Leu Gln Leu Ala Arg Leu Val Glu Gly Leu
65                  70                  75                  80

Ala Gln Val Pro Gln Gly His Cys Glu Glu His Leu Asp Pro Leu Ser
                85                  90                  95

Ile Tyr Cys Glu Gln Asp Arg Ala Leu Val Cys Gly Val Cys Ala Ser
            100                 105                 110

Leu Gly Ser His Arg Gly His Arg Leu Leu Pro Ala Ala Glu Ala His
        115                 120                 125

Ala Arg Leu Lys Thr Gln Leu Pro Gln Gln Lys Leu Gln Leu Gln Glu
    130                 135                 140

Ala Cys Met Arg Lys Glu Lys Ser Val Ala Val Leu Glu His Gln Leu
145                 150                 155                 160

Val Glu Val Glu Glu Thr Val Arg Gln Phe Arg Gly Ala Val Gly Glu
                165                 170                 175

Gln Leu Gly Lys Met Arg Val Phe Leu Ala Ala Leu Glu Gly Ser Leu
            180                 185                 190

Asp Arg Glu Ala Glu Arg Val Arg Gly Glu Ala Gly Val Ala Leu Arg
        195                 200                 205

Arg Glu Leu Gly Ser Leu Asn Ser Tyr Leu Glu Gln Leu Arg Gln Met
    210                 215                 220

Glu Lys Val Leu Glu Glu Val Ala Asp Lys Pro Gln Thr Glu Phe Leu
225                 230                 235                 240

Met Lys Tyr Cys Leu Val Thr Ser Arg Leu Gln Lys Ile Leu Ala Glu
                245                 250                 255

Ser Pro Pro Pro Ala Arg Leu Asp Ile Gln Leu Pro Ile Ile Ser Asp
            260                 265                 270

-continued

```
Asp Phe Lys Phe Gln Val Trp Arg Lys Met Phe Arg Ala Leu Met Pro
        275                 280                 285

Ala Leu Glu Glu Leu Thr Phe Asp Pro Ser Ala His Pro Ser Leu Val
        290                 295                 300

Val Ser Ser Ser Gly Arg Arg Val Glu Cys Ser Glu Gln Lys Ala Pro
305                 310                 315                 320

Pro Ala Gly Glu Asp Pro Arg Gln Phe Asp Lys Ala Val Ala Val Val
                325                 330                 335

Ala Gln Leu Ser Glu Gly Glu His Tyr Trp Glu Val Glu Val Gly Asp
                340                 345                 350

Lys Pro Arg Trp Ala Leu Gly Val Ile Ala Ala Glu Ala Ser Arg Arg
        355                 360                 365

Gly Arg Leu His Ala Val Pro Ser Gln Gly Leu Trp Leu Leu Gly Leu
    370                 375                 380

Arg Glu Gly Lys Ile Leu Glu Ala His Val Glu Ala Lys Glu Pro Arg
385                 390                 395                 400

Ala Leu Arg Thr Pro Glu Arg Arg Pro Thr Arg Ile Gly Leu Tyr Leu
                405                 410                 415

Ser Phe Gly Asp Gly Val Leu Ser Phe Tyr Asp Ala Ser Asp Ala Asp
                420                 425                 430

Ala Leu Pro Leu Phe Ala Phe His Glu Arg Leu Pro Gly Pro Val Tyr
            435                 440                 445

Pro Phe Phe Asp Val Cys Trp His Asp Lys Gly Lys Asn Ala Gln Pro
    450                 455                 460

Leu Leu Leu Val Gly Pro Glu Val Ser Gly Gly Ser Gly Glu Glu Ala
465                 470                 475                 480
```

SERUM MG53 AS A DIAGNOSTIC MARKER FOR TISSUE INJURY

CROSS-REFERENCE TO RELATED APPLICATIONS

This application claims the benefit under 35 U.S.C. §119(e) of U.S. Provisional Applications No. 61/410,430 filed Nov. 5, 2010, which is hereby incorporated by reference in its entirety for all purposes.

INCORPORATION BY REFERENCE

In compliance with 37 C.F.R. §1.52(e)(5), a Computer Readable version of the Sequence Listing containing SEQ ID NOs: 1-13 has been filed electronically, herewith, on file: Weisleder_2011_ST25.txt; size 49 KB; created on: Nov. 2, 2011; using PatentIn-3.5.1, and Checker 4.4.0, which is hereby incorporated by reference in its entirety.

FIELD OF THE INVENTION

Described are diagnostic compositions and methods for measuring biomarkers of tissue damage.

BACKGROUND

Plasma membrane repair is a highly conserved mechanism that appears in nearly every eukaryotic organism, from single cell amoebas to most cell types in the human body. It is a prerequisite for development of complex cellular systems and organelle function, for maintenance of cellular integrity following disruption of the lipid bilayer. An ancient primordial cell would not be able to develop the metabolic resources necessary to produce more sophisticated intracellular organelles if any disruption of the external cell membrane resulted in the death of the cell. While a simple lipid bilayer will reseal through thermodynamic principles, establishment of a cytoskeleton network necessitates that the bilayer bordering the cell be held under some degree of tension. When it is held under tension even small disruptions of a lipid bilayer cannot spontaneously reseal (Togo, T., Krasieva, T. B. & Steinhardt, R. A. A decrease in membrane tension precedes successful cell-membrane repair. Mol Biol Cell 11, 4339-46 (2000)), thus intracellular resealing mechanisms must exist to allow for development of complex cellular systems. Multicellular organisms benefit from the capacity to repair cell membranes, particularly in long lived animals where loss of cellular viability could lead to progression of a disease state, such as the heart and brain where there is limited regenerative capacity.

While membrane repair is a conserved mechanism essential for evolutionary development and maintenance of sensitive organs in humans, the pathways facilitating this process are poorly understood. Little, if anything, is known about the mechanism(s) of how a cell repairs disruptions of the plasma membrane. This is not because membrane repair is not common or unimportant; it is simply due to the lack of understanding of the cellular and molecular machinery that regulates this process. While some cells cope with damage to the plasma membrane by death and replacement, many previous studies indicate that repair of acute damage to the plasma membrane is an important aspect of normal cellular physiology (McNeil, P. L. & Ito, S. Gastrointestinal cell plasma membrane wounding and resealing in vivo. Gastroenterology 96, 1238-48 (1989); McNeil, P. L. & Steinhardt, R. A. Plasma membrane disruption: repair, prevention, adaptation. Annu Rev Cell Dev Biol 19, 697-731 (2003)), and disruption of this process can result in a number of different diseases, including muscular dystrophy, heart failure and neurodegeneration (Bansal, D. et al. Defective membrane repair in dysferlin-deficient muscular dystrophy. Nature 423, 168-72 (2003); Bazan, N. G., Marcheselli, V. L. & Cole-Edwards, K. Brain response to injury and neurodegeneration: endogenous neuroprotective signaling. Ann N Y Acad Sci 1053, 137-47 (2005); Han, R. et al. Dysferlin-mediated membrane repair protects the heart from stress-induced left ventricular injury. J Clin Invest 117, 1805-13 (2007)).

Previous studies established the basic framework of the plasma membrane repair response (McNeil, P. L. & Steinhardt, R. A. Plasma membrane disruption: repair, prevention, adaptation. Annu Rev Cell Dev Biol 19, 697-731 (2003)). It is known that this process requires the translocation of intracellular vesicles (Miyake, K. & McNeil, P. L. Vesicle accumulation and exocytosis at sites of plasma membrane disruption. J Cell Biol 131, 1737-45 (1995)) to the injury site through the action of kinesin and myosin motor proteins. These vesicles then fuse with the plasma membrane in a $Ca^{2+}$ dependent manner to form a repair "patch", a process similar to the release of neurotransmitters from neurons (Steinhardt, R. A., Bi, G. & Alderton, J. M. Cell membrane resealing by a vesicular mechanism similar to neurotransmitter release. Science 263, 390-3 (1994)). Thus, this repair process can be divided into discreet steps involving the; 1) sensing of membrane damage, 2) translocation of vesicles to the injury site, and 3) fusion of vesicles with the plasma membrane. However, the molecular machinery involved in the cellular repair process is not well defined.

Recent studies have identified some molecular components of cell membrane repair, particularly those involved in a pathway thought to be specific to striated muscles. One major finding was our recent discovery that MG53, a muscle-specific TRIM family protein (TRIM72), is an essential component of the acute membrane repair machinery (Cai, C. et al. MG53 nucleates assembly of cell membrane repair machinery. Nat Cell Biol 11, 56-64 (2009); Weisleder, N., Takeshima, H. & Ma, J. Mitsugumin 53 (MG53) facilitates vesicle trafficking in striated muscle to contribute to cell membrane repair. Communicative & Integrative Biology 2, In Press (2009); Cai, C. et al. MG53 regulates membrane budding and exocytosis in muscle cells. J Biol Chem 284, 3314-22 (2009); Cai, C. et al. Membrane repair defects in muscular dystrophy are linked to altered interaction between MG53, caveolin-3, and dysferlin. J Biol Chem 284, 15894-902 (2009)). MG53 acts as a sensor of oxidation to oligomerize and then recruit intracellular vesicles to the injury site for membrane patch formation. We found that MG53 can interact with dysferlin, another protein involved in membrane repair, to facilitate its membrane repair function, and the membrane trafficking function of MG53 can be modulated through a functional interaction with caveolin-3 (Cav3) (Cai, C. et al. MG53 regulates membrane budding and exocytosis in muscle cells. J Biol Chem 284, 3314-22 (2009); Cai, C. et al. Membrane repair defects in muscular dystrophy are linked to altered interaction between MG53, caveolin-3, and dysferlin. J Biol Chem 284, 15894-902 (2009)). Our data indicate that maintenance of the MG53-dysferlin-Cav3 molecular complex is essential for repair of the muscle cell membrane and that disruption of these interactions can results in muscular dystrophy and cardiac dysfunction.

Our published findings show that elevated MG53 expression within a cell can increase resistance to cellular disruption, however there are obvious hurdles in controlling MG53 expression in an organism as a therapeutic approach. However, it was also discovered that placing recombinant MG53 protein outside of the cell can increase the capacity of both muscle and non-muscle plasma membranes to reseal following damage. Direct proof-of-concept studies for the therapeutic use of recombinant MG53 as a membrane repair reagent were based on strong in vitro and in vivo animal model studies, which were detailed in two previous patent applications (PCT/US2007/015815 and PCT/US2008/085573). Recombinant MG53 was found to be highly effective at increasing membrane repair in skeletal muscle, cardiac muscle, epithelial cells and several other cell types. These results indicate that isolated MG53 protein can be applied externally to many different cell types and it will target to sites of membrane damage increase membrane resealing, preventing pathology and improving the structure and function of the tissue.

Herein, we present for the first time data indicating that endogenous MG53 can be detected in circulating blood, and that the level of MG53 in blood serum varies in control (i.e., normal) versus disease. As such, MG53 can be used as a diagnostic biomarker for tissue injury. Moreover, targeting serum MG53 can be a potential therapeutic means for treatment of tissue injury in human diseases.

SUMMARY

The description relates to the surprising and unexpected discovery that MG53 and/or a portion thereof (collectively, "MG53") can be detected in the circulating blood. Moreover, the amount of MG53 varies between normal or healthy subjects versus subjects suffering from a pathological condition, e.g., a muscle-related disease or disorder. Thus, in certain aspects, the description provides methods for detecting an MG53 polypeptide in a biological fluid of a subject. In certain embodiments, the presence and/or amount of the polypeptide is indicative of a subject suffering from a pathological condition, e.g., tissue damage or muscle-related disease or disorder.

As such the detection of MG53 or portions thereof in the blood or serum of a subject are useful for, e.g., 1) determining if a disease or disorder (e.g., muscle-related disease or disorder) exists; 2) determining if the disease or disorder can be treated by an agent or combination of agents; 3) selecting an appropriate agent or combination of agents for treating the disease or disorder; 4) monitoring the disease or disorder; 5) monitoring the effectiveness of an ongoing treatment, 6) identifying new treatments (single agent or combination of agents); 7) predicting a subject's clinical outcome; and 8) monitoring performance during exercise. In particular, MG53 may be utilized as a marker (surrogate and/or direct) to determine appropriate therapy, to monitor clinical therapy and human trials of a drug being tested for efficacy, and to develop new agents and therapeutic combinations.

In additional aspects, the description provides agents, e.g., probes, capable of specifically binding to MG53 and/or portions thereof or both. In certain embodiments, the agent or probe is an antibody capable of specifically binding to MG53 and/or a portion thereof or both.

In an additional aspect, the description provides agents, e.g., anti-MG53 antibodies, for use in manufacturing of a composition for performing a method as described herein.

In an additional aspect, the description provides agents, e.g., anti-MG53 antibodies, for use in a method as described herein.

In an additional aspect, the description provides kits comprising an agent or probe capable of specifically binding to MG53, and directions for performing a diagnostic method as described herein.

Additional advantageous features and functionalities associated with the compositions, methods, and processes of the present invention will be apparent from the drawings presented herein, as well as the detailed description which follows. The publications and other materials used herein to illuminate the background of the invention, and in particular cases, to provide additional details respecting the practice, are incorporated by reference, and for convenience are listed in the appended bibliography.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention.

FIG. 3. MG53 is released from cardiac tissues following ischemia/reperfusion injury to the heart. (a) A western blot for the presence of MG53 in samples of perfusion buffer from a Langendorff perfused wild type (C57BL/10J) mouse heart at indicated times following reperfusion after 30 minutes of global ischemia. The mouse heart was perfused with Kreb's buffer for an equilibration period of 30 minutes, then all flow was ceased for 30 minutes followed by reperfusion for 1 hour. Perfusates were collected last 10 minutes of equilibration as baseline, then at intervals of 0-1', 1'-2', 2'-3', 3'-5', 5'-10', 10'-20', 20'-30', 30-40', 40'-50', 50'-60'. Perfusates were concentrated 10 times by centrifugation concentration membrane units. (b) Creatine kinase (CK) levels were also measured for the same samples using an enzyme activity kit. There is a correlation between the levels of CK and MG53 following this injury to the heart.

FIG. 5. Native MG53 in serum samples can be detected through the use of ELISA assays. (a) To determine if an ELISA assay can detect recombinant MG53 we generated a sandwich ELISA using the mouse monoclonal antibody 5259 (40 ug/ml) as a capture antibody and a rabbit affinity purified polyclonal anti-MG53 Ab (1:500) as a detection antibody. A HRP-conjugated anti-rabbit IgG antibody (1:1000) was used to develop the ELISA. Recombinant human MG53 protein was applied to this assay at various concentrations (as indicated) where a dose-dependent signal could be seen in the ELISA assay. (b) Mouse serum samples from exercised MG53 knockout (MG53−/−), as a negative control, and mdx mice, as a positive control, were applied to the ELISA assay (20 ul each well). While the MG53−/− serum matched a no-protein control (PBS) there was a great increase in signal with the mdx serum, indicating that an ELISA can be used to detect native MG53 levels in serum.

DETAILED DESCRIPTION

Figure 1:
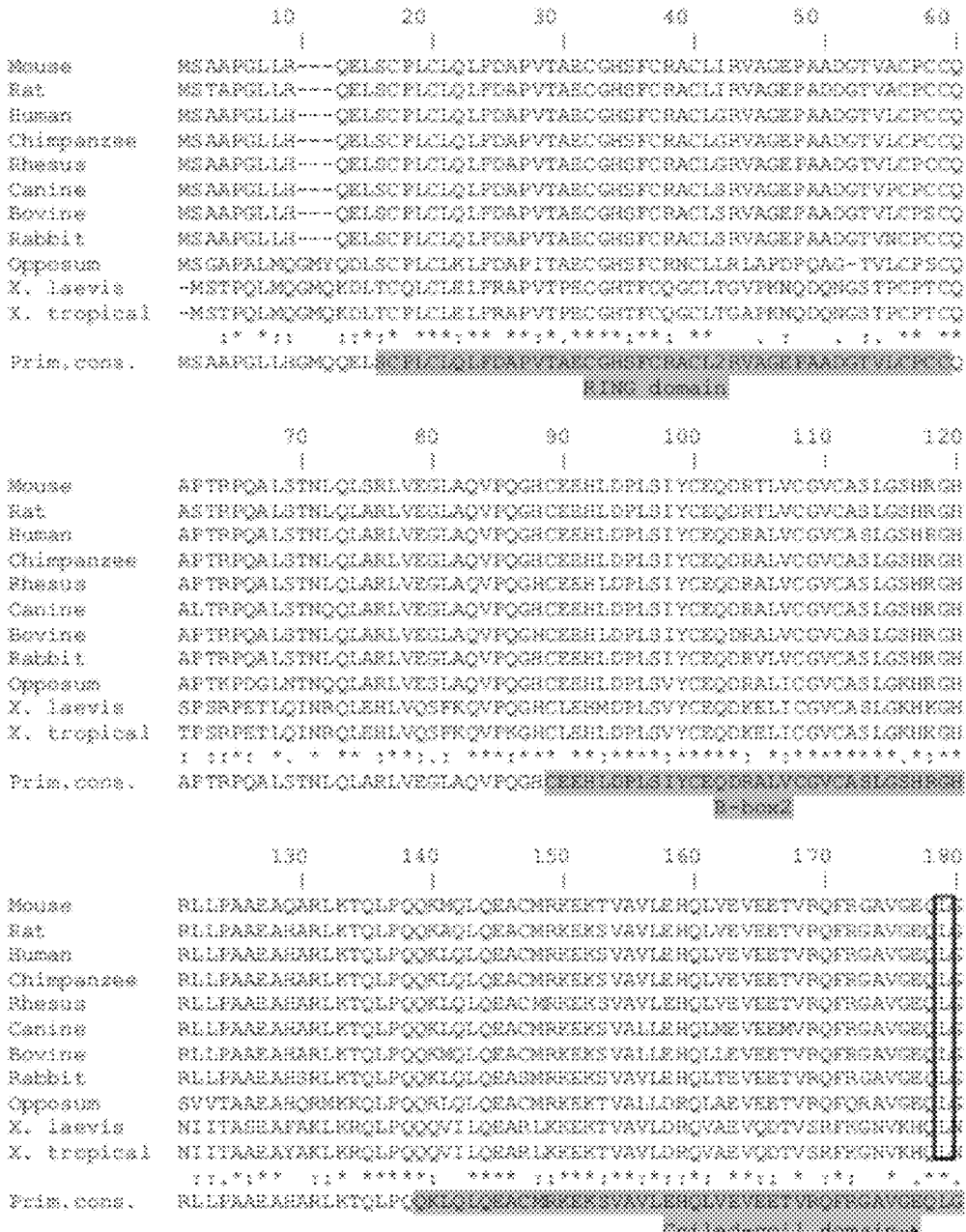
FIG. 1. MG53 is a muscle specific member of the TRIM protein family. An alignment of the protein sequence of MG53 from various organisms (See SEQ ID NOs.: 1, 3, 5-13) reveals this protein to be a member of the TRIM family. Functional domains are boxed in grey while arrows indicate the domain continues onto another line of the sequence.

The following is a detailed description of the invention provided to aid those skilled in the art in practicing the present invention. Those of ordinary skill in the art may make modifications and variations in the embodiments described herein without departing from the spirit or scope of the present invention. Although any methods and materials similar or equivalent to those described herein can also be used in the practice or testing of the present invention, the preferred methods and materials are now described. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Mitsugumin53 (MG53) is a muscle-specific tri-partite motif (TRIM) family protein capable of facilitating the repair of cell membranes. See U.S. Pat. No. 7,981,866; PCT/US2007/015815; and PCT/US2008/085573, which are incorporated by reference in their entirety for all purposes. Previously, the inventors discovered that MG53 expression facilitates intracellular vesicle trafficking to and fusion with the plasma membrane. In addition, vesicular fusion during acute membrane repair is driven by MG53, homologs, analogs, and fragments derived therefrom (herein, collectively, "MG53") (see, e.g., SEQ ID NOs.: 1-13). Surprisingly, it was discovered that MG53 proteins, homologs, analogs, and fragments derived therefrom, (herein, collectively, "MG53;" see, e.g., SEQ ID NOs.: 1-13) are capable of facilitating membrane repair even when present on the outside of a cell.

Presently, it has been surprisingly and unexpectedly discovered that MG53 can be detected in the circulating blood or serum of a subject. Moreover, the presence and/or amount of MG53 varies between normal or healthy subjects versus subjects suffering from a pathological condition, e.g., tissue damage or a muscle-related disease or disorder. Thus, in certain aspects, the description provides diagnostic methods for detecting an MG53 polypeptide in a biological fluid isolated from a subject.

As used herein, the following terms may have meanings ascribed to them below, unless specified otherwise. However, it should be understood that other meanings that are known or understood by those having ordinary skill in the art are also possible, and within the scope of the present invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless indicated otherwise, "MG53" is used generally to refer to MG53, MG53 homologs, MG53-derived polypeptides, including mutants, fragments, portions, and epitopes thereof, as explicitly, implicitly, or inherently described herein.

It must be noted that as used herein and in the appended claims, the singular forms "a", "and", and "the" include plural references (i.e., refer to one or to more than one or at least one) to the grammatical object of the article. By way of example, "an element" means one element or more than one element.

The term "about" as it is used herein, in association with numeric values or ranges, reflects the fact that there is a certain level of variation that is recognized and tolerated in the art due to practical and/or theoretical limitations. For example, minor variation is tolerated due to inherent variances in the manner in which certain devices operate and/or measurements are taken. In accordance with the above, the phrase "about" is normally used to encompass values within the standard deviation or standard error.

As used herein, "derivatives" are compositions formed from the native compounds either directly, by modification, or by partial substitution. As used herein, "analogs" are compositions that have a structure similar to, but not identical to, the native compound.

The term "polypeptides" can mean, but is in no way limited to, recombinant full length, pro- and/or mature polypeptide forms as well as the biologically active forms, including fragments or splice variants, or recombinantly made truncations or portions derived from the full length polypeptides. Furthermore, polypeptides of the invention may include amino acid mimentics, and analogs. Recombinant forms of the chimeric polypeptides can be produced according to standard methods and protocols which are well known to those of skill in the art, including for example, expression of recombinant proteins in prokaryotic and/or eukaryotic cells followed by one or more isolation and purification steps, and/or chemically synthesizing cytokine polypeptides or portions thereof using a peptide sythesizer.

The term "effective amount/dose," "pharmaceutically effective amount/dose," "pharmaceutically effective amount/dose" or "therapeutically effective amount/dose" can mean, but is in no way limited to, that amount/dose of the active pharmaceutical ingredient sufficient to prevent, inhibit the occurrence, ameliorate, delay or treat (alleviate a symptom to some extent, preferably all) the symptoms of a condition, disorder or disease state. The effective amount depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 1000 mg/kg body weight/day of active ingredients is administered dependent upon potency of the agent. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The term "pharmacological composition," "therapeutic composition," "therapeutic formulation" or "pharmaceutically acceptable formulation" can mean, but is in no way limited to, a composition or formulation that allows for the effective distribution of an agent provided by the invention, which is in a form suitable for administration to the physical location most suitable for their desired activity, e.g., systemic administration.

The term "pharmaceutically acceptable" or "pharmacologically acceptable" can mean, but is in no way limited to, entities and compositions that do not produce an adverse, allergic or other untoward reaction when administered to an animal, or a human, as appropriate.

The term "pharmaceutically acceptable carrier" or "pharmacologically acceptable carrier" can mean, but is in no way limited to, any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The term "systemic administration" refers to a route of administration that is, e.g., enteral or parenteral, and results in the systemic distribution of an agent leading to systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect. Administration routes which lead to systemic absorption include, without limitations: intravenous, subcutaneous, intraperitoneal, inhalation, oral, intrapulmonary and intramuscular. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful.

The term "local administration" refers to a route of administration in which the agent is delivered to a site that is apposite or proximal, e.g., within about 10 cm, to the site of the lesion or disease.

The term "nucleotide" can mean, but is no way limited to, a heterocyclic nitrogenous base in N-glycosidic linkage with a phosphorylated sugar. Nucleotides are recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; Uhlman & Peyman, supra all are hereby incorporated by reference herein). There are several examples of modified nucleic acid bases known in the art as summarized by Limbach et al., 1994, Nucleic Acids Res. 22, 2183. Some of the non-limiting examples of chemically modified and other natural nucleic acid bases that can be introduced into nucleic acids include, for example, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetyltidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio- N6-isopentenyladenosine, beta-D-mannosylqueosine, uridine-5-oxyacetic acid, 2-thiocytidine, threonine derivatives and others (Burgin et al., 1996, Biochemistry, 35, 14090; Uhlman & Peyman, supra).

The term "nucleic acid" or "polynucleotide" can mean, but is in no way limited to, a molecule having more than one nucleotide, and is intended to include DNA molecules (e.g., cDNA or genomic DNA), RNA molecules, analogs of DNA or RNA, including locked nucleic acids and peptide nucleic acids, and derivatives thereof. The nucleic acid can be single, double, or multiple stranded and can comprise modified or unmodified nucleotides or non-nucleotides or various mixtures and combinations thereof. The nucleic acids of the invention are added directly, or can be complexed with cationic lipids, packaged within liposomes, or otherwise delivered to target cells or tissues. The nucleic acid or nucleic acid complexes can be locally administered to relevant tissues in vitro, ex vivo, or in vivo through injection or infusion pump, with or without their incorporation in biopolymers.

A polynucleotide can be a DNA molecule, a cDNA molecule, genomic DNA molecule, or an RNA molecule. A polynucleotide as DNA or RNA can include a sequence wherein T (thymidine) can also be U (uracil). If a nucleotide at a certain position of a polynucleotide is capable of forming a Watson-Crick pairing with a nucleotide at the same position in an anti-parallel DNA or RNA strand, then the polynucleotide and the DNA or RNA molecule are complementary to each other at that position. The polynucleotide and the DNA or RNA molecule are substantially complementary to each other when a sufficient number of corresponding positions in each molecule are occupied by nucleotides that can hybridize with each other in order to effect the desired process.

The term "derivatives" can mean, but is in no way limited to, chemical compositions, for example, nucleic acids, nucleotides, polypeptides or amino acids, formed from the native compounds either directly, by modification, or by partial substitution. The term "analogs" can mean, but is in no way limited to, chemical compositions, for example, nucleic acids, nucleotides, polypeptides or amino acids that have a structure similar to, but not identical to, the native compound.

The term "hybridization" can mean, but is in no way limited to, the binding, duplexing, or hybridizing of a molecule only to a particular nucleotide sequence under low, medium, or highly stringent conditions, including when that sequence is present in a complex mixture (e.g., total cellular) DNA or RNA.

The term "conservative mutations" refers to the substitution, deletion or addition of nucleic acids that alter, add or delete a single amino acid or a small number of amino acids in a coding sequence where the nucleic acid alterations result in the substitution of a chemically similar amino acid. Amino acids that may serve as conservative substitutions for each other include the following: Basic: Arginine (R), Lysine (K), Histidine (H); Acidic: Aspartic acid (D), Glutamic acid (E), Asparagine (N), Glutamine (Q); hydrophilic: Glycine (G), Alanine (A), Valine (V), Leucine (L), Isoleucine (I); Hydrophobic: Phenylalanine (F), Tyrosine (Y), Tryptophan (W); Sulfur-containing: Methionine (M), Cysteine (C). In addition, sequences that differ by conservative variations are generally homologous.

The term "down-regulate" can mean, but is in no way limited to, the expression of the gene, or level of RNAs or equivalent RNAs encoding one or more proteins, amount and/or activity of one or more proteins is reduced below that observed in the absence of an agent provided by the invention. For example, the expression of a gene can be decreased in order to treat, prevent, ameliorate, or modulate a pathological condition caused or exacerbated by high levels of gene expression.

The term "up-regulate" can mean, but is in no way limited to, the expression of the gene, or level of RNAs or equivalent RNAs encoding one or more proteins, amount and/or activity of one or more proteins is greater than that observed in the absence of an agent provided by the invention. For example, the expression of a gene can be increased in order to treat, prevent, ameliorate, or modulate a pathological condition caused or exacerbated by an absence or low level of gene expression.

By "modulate" is meant that the expression of the gene, or level of RNAs or equivalent RNAs encoding one or more proteins, amount and/or activity of one or more proteins is up-regulated or down-regulated, such that the expression, level, or activity is greater than or less than that observed in the absence of an agent provided by the invention.

The term, "gene" can mean, but is in no way limited to, a nucleic acid that encodes RNA, for example, nucleic acid sequences including but not limited to a segment encoding a polypeptide. Unless otherwise indicated, the term "gene" is used in a general sense to refer to the genomic and/or cDNA forms of a nucleic acid encoding a polypeptide.

The term "complementarity" can mean, but is in no way limited to, the ability of a nucleic acid to form hydrogen bond(s) with another RNA sequence by either traditional Watson-Crick, Hoogsteen base pairing or other non-traditional types.

The term "binding" can mean, but is in no way limited to, the physical or chemical interaction, direct or indirect, between two molecules (e.g., compounds, amino acids, nucleotides, polypeptides, or nucleic acids). Binding includes covalent, hydrogen bond, ionic, non-ionic, van der Waals, hydrophobic interactions, and the like.

The term "equivalent" or "homologous" can mean, but is in no way limited to, nucleic acids or proteins including those naturally occurring DNA, RNA or amino acid molecules have homology (partial or complete) to an MG53 gene or cDNA (e.g., SEQ ID NOs:2 and 4) or protein (SEQ ID NOs:1, 3, 5-13) with similar function as MG53 in various organisms, including human, rodent, primate, rabbit, pig, protozoans, fungi, plants, and other microorganisms and parasites. The equivalent RNA sequence also includes, in addition to the coding region, regions such as 5'-untranslated region, 3'-untranslated region, introns, intron-exon junction and the like. By "homology" is meant the nucleotide sequence of two or more nucleic acid molecules or two or more nucleic acid or amino acid sequences is partially or completely identical. In certain embodiments the homologous nucleic acid or amino acid sequence has 30%, 40%, 50%, 60%, 70%, 80%, 90%, or 95% sequence similarity or identity to an MG53 gene or protein, respectively. In certain embodiments, the invention provides a nucleic acid having 30%, 40%, 50%, 60%, 70%, 80%, 90%, or 95% similarity or identity to a nucleic acid selected from SEQ ID NOs.:2 or 4. In additional embodiments, the invention provides a polypeptide having 30%, 40%, 50%, 60%, 70%, 80%, 90%, or 95% similarity or identity to polypeptide selected from SEQ ID NOs.: 1, 3, or 5-13 or a portion thereof.

"Homologs" can be naturally occurring, or created by artificial synthesis of one or more nucleic acids having related sequences, or by modification of one or more nucleic acid to produce related nucleic acids. Nucleic acids are homologous when they are derived, naturally or artificially, from a common ancestor sequence (e.g., orthologs or paralogs). If the homology between two nucleic acids is not expressly described, homology can be inferred by a nucleic acid comparison between two or more sequences. If the sequences demonstrate some degree of sequence similarity, for example, greater than about 30% at the primary amino acid structure level, it is concluded that they share a common ancestor. For purposes of the present invention, genes are homologous if the nucleic acid sequences are sufficiently similar to allow recombination and/or hybridization under low stringency conditions. In addition, polypeptides are regarded as homologous if their nucleic acid sequences are sufficiently similar to allow recombination or hybridization under low stringency conditions, and optionally they demonstrate membrane repair activity, and optionally they can be recognized by (i.e., cross-react with) an antibody specific for an epitope contained within the amino acid sequence of at least one of SEQ ID NOs: 1, 3, or 5-13.

As used herein "hybridization," refers to the binding, duplexing, or hybridizing of a molecule only to a particular nucleotide sequence under low, medium, or highly stringent conditions, including when that sequence is present in a complex mixture (e.g., total cellular) DNA or RNA.

The term "RNA" can mean, but is in no way limited to, a molecule comprising at least one ribonucleotide residue. By "ribonucleotide" or "2'-OH" is meant a nucleotide with a hydroxyl group at the 2' position of a D-ribo-furanose moiety.

The term "vectors" can mean, but is in no way limited to, any nucleic acid-based technique used to deliver a desired nucleic acid, for example, bacterial plasmid, viral nucleic acid, HAC, BAC, and the like for cloning, amplification, and/or expression of a gene.

The term "cell" can mean, but is in no way limited to, its usual biological sense, and does not refer to an entire multicellular organism. The cell can, for example, be in vivo, in vitro or ex vivo, e.g., in cell culture, or present in a multicellular organism, including, e.g., birds, plants and mammals such as humans, cows, sheep, apes, monkeys, swine, dogs, and cats. The cell can be prokaryotic (e.g., bacterial cell) or eukaryotic (e.g., mammalian or plant cell).

The term "host cell" can mean, but is in no way limited to, a cell that might be used to carry a heterologous nucleic acid, or expresses a peptide or protein encoded by a heterologous nucleic acid. A host cell can contain genes that are not found within the native (non-recombinant) form of the cell, genes found in the native form of the cell where the genes are modified and re-introduced into the cell by artificial means, or a nucleic acid endogenous to the cell that has been artificially modified without removing the nucleic acid from the cell. A host cell may be eukaryotic or prokaryotic. General growth conditions necessary for the culture of bacteria can be found in texts such as BERGEY'S MANUAL OF SYSTEMATIC BACTERIOLOGY, Vol. 1, N. R. Krieg, ed., Williams and Wilkins, Baltimore/London (1984). A "host cell" can also be one in which the endogenous genes or promoters or both have been modified to produce one or more of the polypeptide components of the complex of the invention.

As used herein, a "marker" or "biomarker" is a naturally-occurring polymer corresponding to at least one of the polypeptides or nucleic acids of SEQ ID NOs:1-13 or portion thereof. For example, markers include, without limitation, sense and anti-sense strands of genomic DNA (i.e. including any introns occurring therein), RNA generated by transcription of genomic DNA (i.e. prior to splicing), RNA generated by splicing of RNA transcribed from genomic DNA, and proteins generated by translation of spliced RNA (i.e. including proteins both before and after cleavage of normally cleaved regions such as transmembrane signal sequences). As used herein, "marker" may also include a cDNA made by reverse transcription of an RNA generated by transcription of genomic DNA (including spliced RNA).

The term "probe" refers to any molecule which is capable of selectively binding to a specifically intended target molecule, for example a marker of the invention. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic monomers.

The "normal" level of a marker is the level of the marker in a biological sample of a patient not afflicted with the disease or disorder.

A marker or a probe is "fixed" to a substrate if it is covalently or non-covalently associated with the substrate such the substrate can be rinsed with a fluid without a substantial fraction of the marker or probe dissociating from the substrate.

A marker in a patient is "significantly" higher or lower than the normal level of the marker if the level of the marker is greater or less, respectively, than the normal level by an amount greater than the standard error of the assay employed, and preferably at least twice, and more preferably three, four, five or ten times that amount.

As used herein, "inhibited" refers to, but is not limited to, a reduced, slowed, delayed, or prevention of a disease or disorder.

As used herein, the term "agent" is defined broadly as any therapeutic agent. The agents tested in the present methods can be a single agent or a combination of agents. For example, the present methods can be used to determine whether a single agent can be used to treat a disease or disorder or whether a combination of two or more agents can be used. Preferred combinations will include agents that have different mechanisms of action A subject (cell, tissue, or patient) is "sensitive" to a therapeutic agent if contact with a therapeutic agent causes an effect, compared to the absence of contact with the therapeutic agent. The quality of being sensitive to a therapeutic agent is a variable one, with different levels of "sensitivity" to a given therapeutic agent, under different conditions being possible. In one embodiment of the invention, a subject may be predisposed to sensitivity to an agent if the corresponding sensitivity marker is present.

The term "diagnosing" includes the use of the methods, and systems as described herein to determine the presence or absence of a disease or disorder, e.g., tissue injury or muscle-related disorder in an individual. The term also includes methods, and systems for assessing the level of disease activity in an individual. In some embodiments, statistical algorithms are used to diagnose a mild, moderate, severe, or fulminant form of a disease or disorder, e.g., tissue injury or muscle-related disorder in an individual. One skilled in the art will know of other methods for evaluating the severity of diseases and disorders in an individual.

The term "monitoring the progression or regression" includes the use of the methods, and systems as described herein to determine the disease state (e.g., presence or severity of a disease or disorder, e.g., tissue injury or muscle-related disorder) of an individual. In certain instances, the results of a statistical algorithm (e.g., a learning statistical classifier system) are compared to those results obtained for the same individual at an earlier time. In some aspects, the methods, systems, and code of the present invention can also be used to predict the progression of a disease or disorder, e.g., by determining a likelihood for the disease or disorder to progress either rapidly or slowly in an individual based on the presence or level of at least one marker in a sample. In other aspects, the methods, and systems as described herein can also be used to predict the regression of a disease or disorder, e.g., by determining a likelihood for a disease or disorder to regress either rapidly or slowly in an individual based on the presence or level of at least one marker in a sample.

The term "monitoring drug efficacy in an individual receiving a drug useful for treating a disease or disorder" includes the use of the methods, and systems as described herein to determine the disease state (e.g., presence or severity of a disease or disorder) of an individual after a therapeutic agent has been administered. In certain instances, the results of a statistical algorithm (e.g., a learning statistical classifier system) are compared to those results obtained for the same individual before initiation of use of the therapeutic agent or at an earlier time in therapy. As used herein, a drug useful for treating a disease or disorder is any compound or drug used to improve the health of the individual.

The term "optimizing therapy in an individual" includes the use of the methods, and systems as described herein to determine the course of therapy for an individual before a therapeutic agent (e.g., to treat tissue injury or muscle-related disease or disorder) has been administered or to adjust the course of therapy for an individual after a therapeutic agent has been administered in order to optimize the therapeutic efficacy of the therapeutic agent. In certain instances, the results of a statistical algorithm (e.g., a learning statistical classifier system) are compared to those results obtained for the same individual at an earlier time during the course of therapy. As such, a comparison of the results provides an indication for the need to change the course of therapy or an indication for the need to increase or decrease the dose of the current course of therapy.

The term "course of therapy" includes any therapeutic approach taken to relieve or prevent one or more symptoms (i.e., clinical factors) associated with a disease or disorder. The term encompasses administering any compound, drug, procedure, or regimen useful for improving the health of an individual and includes any of the therapeutic agents as well as surgery. One skilled in the art will appreciate that either the course of therapy or the dose of the current course of therapy can be changed, e.g., based upon the results of a statistical algorithm (e.g., a learning statistical classifier system).

The term "therapeutically effective amount or dose" includes a dose of a drug that is capable of achieving a therapeutic effect in a subject in need thereof. For example, a therapeutically effective amount of a drug can be the amount that is capable of preventing or relieving one or more symptoms associated with a disease or disorder, e.g., tissue injury or muscle-related disease or disorder. The exact amount can be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

A kit is any manufacture (e.g. a package or container) comprising at least one reagent, e.g. a probe, for specifically detecting a marker of the invention. The manufacture may be promoted, distributed, or sold as a unit for performing the methods of the present invention. The reagents included in such a kit comprise probes/primers and/or antibodies for use in detecting sensitivity and resistance gene expression. In addition, the kits of the present invention may preferably contain instructions which describe a suitable detection assay. Such kits can be conveniently used, e.g., in clinical settings, to diagnose patients exhibiting symptoms of cancer, in particular patients exhibiting the possible presence of a tumor.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In the case of conflict, the present specification, including definitions, will control. In addition, the materials, methods, and examples are illustrative only and not intended to be limiting.

The following references, the entire disclosures of which are incorporated herein by reference, provide one of skill with a general definition of many of the terms used in this invention: Singleton et al., Dictionary of Microbiology and Molecular Biology ($2^{nd}$ ed. 1994); The Cambridge Dictionary of Science and Technology (Walker ed., 1988); The Glossary of Genetics, $5^{th}$ Ed., R. Rieger et al. (eds.), Springer Verlag (1991); and Hale & Marham, the Harper Collins Dictionary of Biology (1991).

Identification of MG53 as a Biomarker

Is has been surprisingly and unexpectedly discovered that MG53 can be detected in the circulating blood and the amount of MG53 varies between normal or healthy subjects versus subjects suffering from a pathological condition, e.g., a muscle-related disease or disorder. Thus, the present description provides a marker whose presence in blood or serum correlates with a pathological condition, e.g., tissue damage or a muscle-related disease or disorder. Accordingly, MG53 can be used as a marker (or surrogate marker) to identify pathological conditions or predisposition to the same, and/or identify subjects that can be successfully treated by a therapeutic agent. In addition, MG53 proteins can be used to identify conditions that have become or are at risk of becoming refractory to treatment with the agent.

MG53 is a muscle-specific protein that contains TRIM and SPRY motifs. In previous studies we have established a monoclonal antibody (mAb) library that targets proteins associated with the triad junction in skeletal muscle. Screening of this immuno-proteomic library for muscle specific proteins led to the identification of an antigen named MG53 with a molecular size of 53 kilodaltons (kDa), which was recognized by mAb5259. MG53 was partially purified from rabbit skeletal muscle by an immunoaffinity column conjugated with mAb5259, and subjected to amino acid sequencing. Based on the obtained partial amino acid sequences, cDNAs encoding MG53 were isolated from rabbit and mouse skeletal muscle libraries. Genomic library search identified the corresponding MG53 gene on the human 16p11.2 locus. The predicted amino acid sequences for MG53 in several species are shown in FIG. 1.

Domain homology analysis revealed that MG53 contains the prototypical TRIM signature sequence of RBCC plus a SPRY domain at the carboxyl-terminus, and thus belongs to the TRIM/RBCC family (FIG. 1). Of the approximately 60 TRIM family members so far identified in the mammalian genomes, 15 members carry a similar SPRY domain following the RBCC domain, and MG53 shows a conserved primary structure with these TRIM sub-family proteins. However, surprisingly and unexpectedly our studies indicate that MG53 is the only TRIM family protein of those in that demonstrate membrane repair function.

MG53 and portions thereof are particularly useful in the methods of the present invention. Many intracellular soluble proteins normally found in the myoplasm of striated muscle cells appear in the bloodstream of animals and humans at low levels during rest and at elevated levels following stress events known to damage the sarcolemmal membrane, such as eccentric exercise or ischemia/reperfusion (I/R) injury. Levels of the muscle specific proteins creatine kinase (CK) and troponin are commonly used as biomarkers for I/R injury to the heart during a myocardial infarction.

Figure 2:
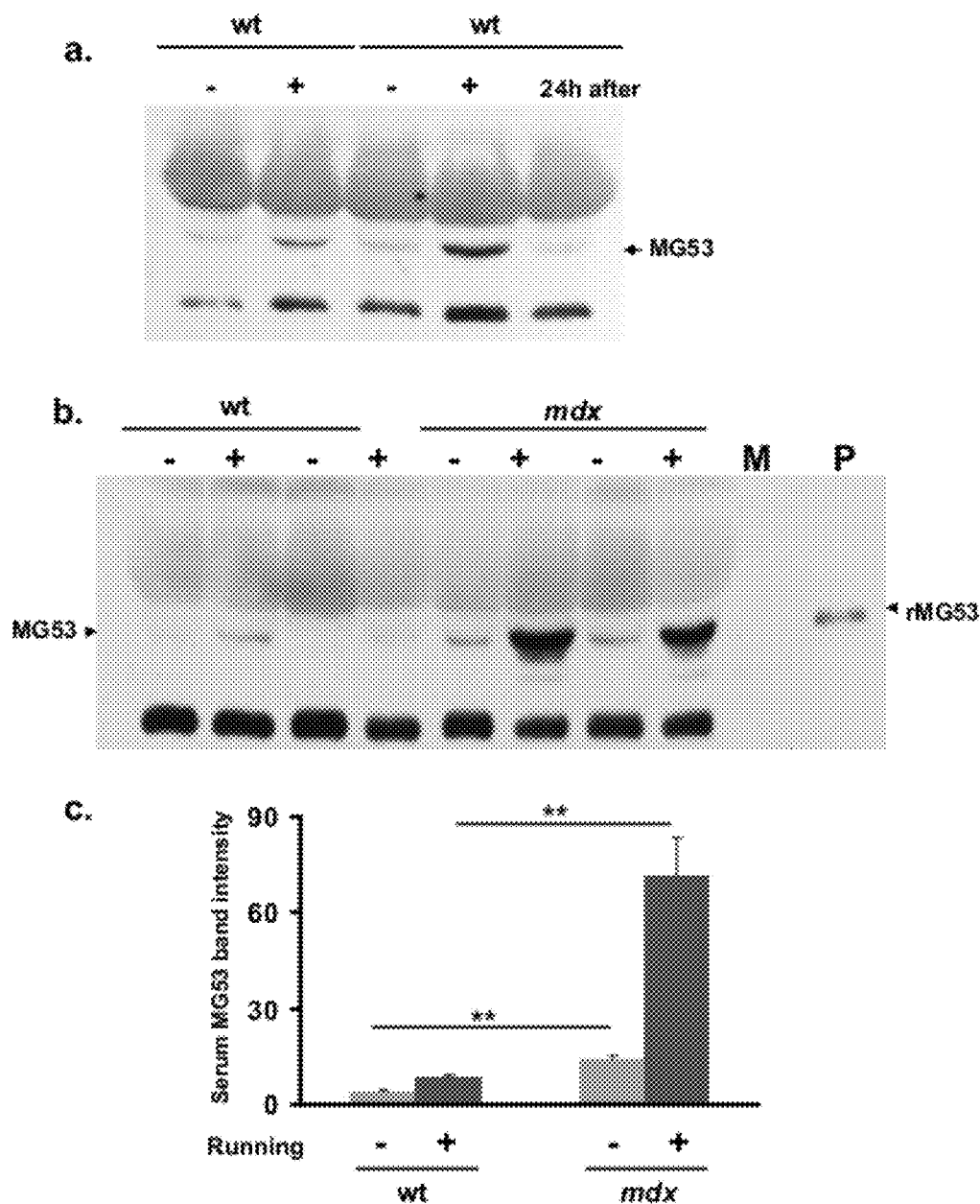
FIG. 2. Levels of native MG53 in the blood increase in dystrophic mice and with exercise. (a) Western blot for appearance of MG53 in mouse serum samples (100 ug total protein) from two wild type (wt) C57BL/10J mice at the resting state at the resting state (−) and following 1.5 hours of 15° downhill treadmill running at 10 m/s (+). Serum MG53 levels were measured in one mouse 24 hours after treadmill running (24 h after). (b) Western blot for appearance of MG53 in mouse serum samples (100 ug total protein) from two wild type (wt) C57BL/10J mice and two dystrophic mice (mdx) at the resting state at the resting state (−) and following 1.5 hours of 15° downhill treadmill running at 10 m/s (+). M indicates the positions of molecular weight markers that do not appear on the western blot. (c) Summary of densitometry data from multiple experiments (n=6 mice per group). Compared to WT mice, mdx mice displayed a higher basal level of serum MG53, and also a significant increase after treadmill running due t of damaged and permeable muscle fibers. **$p<0.01$.

FIG. 2 demonstrates that MG53 is a serum marker capable of assessing a subject's disease status and/or therapeutic sensitivity. To assess if native MG53 could be observed in the bloodstream at the resting state, an MG53 western blot analysis of serum samples isolated from normal (wild type) mice was conducted. It was found that MG53 appears in the blood of the mice at the resting state, and that eccentric exercise produced by downhill treadmill running increases the level of MG53 in the serum (FIG. 2a). After 24 hours, the MG53 released into the blood due to eccentric exercise is cleared from the circulation and serum levels have returned to baseline. This rapid reduction of MG53 suggests that it would make a specific biomarker for muscle damage in human patients.

While levels of MG53 can be observed in the blood of wild type mice, genetically modified mice that develop muscular dystrophy (mdx) related to compromised membrane integrity display significantly more MG53 in the serum (FIG. 2b). This increase in the mdx mice is greatly exacerbated by eccentric exercise to a much greater extent than that seen in the wild type mice. The extent of increase was determined by densitometry measurements that show that mdx had serum MG53 levels elevated above those in wild type mice at basal and exercised conditions (FIG. 2c). Furthermore, downhill running induced significant elevation of serum MG53 in both wild type (2.1±0.8 fold change, n=6; P<0.01) and mdx mice (5.1±0.8, n=6; P<0.01), with an obvious increase in the mdx mice, likely due to fragility of the sarcolemmal membrane in these mice.

During a myocardial infarction, blood flow is blocked in a portion of the coronary circulation and the cardiac tissue that does not received sufficient blood flow will suffer from ischemia. Prolonged ischemia can result in damage to the affected myocardium, however the majority of damage is produced when blood flow is restored in the heart through surgical interventions. This reperfusion of the heart can produce reactive oxygen species that result in peroxidation of the lipids in the sarcolemmal membrane, resulting in breakdown of membrane integrity and death of the cell. This I/R injury results in the release of CK and troponins into the blood, which can then be used as biomarkers for patients experience a myocardial infarction.

To test if MG53 is also released into the coronary circulation during I/R injury to the heart, we used a Langedorff perfusion system to induce global ischemia in isolated mouse hearts. Following a 30 minute global ischemia event, the restoration of perfusion of the heart results in a robust MG53 signal in the perfusate solution when measured by western blot (FIG. 3a). The release of MG53 peaks early after the restoration of perfusion in the heart and the level of MG53 returns to normal within an hour. The kinetics of MG53 appearance in the perfusate is very similar to that seen for CK release in the same hearts (FIG. 3b). This result indicates that MG53 is useful as a serum biomarker for skeletal and cardiac muscle damage in a number of different diseases.

Exemplary Embodiments

The present findings indicate that the detection of MG53 in a biological fluid, e.g., the blood or serum, of a subject is useful for, e.g., 1) determining if a disease or disorder exists, e.g., tissue injury or muscle-related disease or disorder (e.g., muscular dystrophy); 2) determining if a disease or disorder can be treated by an agent or combination of agents; 3) selecting an appropriate agent or combination of agents for treating a disease or disorder; 4) monitoring a disease or disorder; 5) monitoring the effectiveness of an ongoing treatment, 6) identifying new treatments (single agent or combination of agents); and 7) predicting a subject's clinical outcome. "Clinical outcome" refers to a subject's status for the given time period, i.e., disease free or recurrence of disease. In particular, MG53 in blood or serum of a subject may be utilized as a marker (surrogate and/or direct) to determine appropriate therapy, to monitor clinical therapy and human trials of a drug being tested for efficacy, and to develop new agents and therapeutic combinations.

Thus, in certain aspects, the description provides diagnostic methods for detecting an MG53 polypeptide having about 30%, 40%, 50%, 60%, 70%, 80%, 90% or 100% (including values in between) in sequence identity to full-length human MG53 (SEQ ID NO:1) in a biological fluid of a subject. In certain embodiments, the presence and/or amount of the MG53 polypeptide is indicative of a subject suffering from a pathological condition, e.g., having tissue damage or a muscle-related disease or disorder.

In one aspect, the diagnostic method comprises the steps of: a) isolating or obtaining a biological tissue or fluid sample, e.g., blood or serum, from a subject to be tested (i.e., "test sample"), and from a reference or control subject (i.e., "reference sample"); b) determining whether the test sample contains MG53 (i.e., assaying for the presence and/or amount of MG53 in the test sample), c) comparing the presence and/or amount of MG53 in the test sample to the reference sample, wherein an increase or decrease in MG53 over the reference value or control value is indicative of a disease, disorder or syndrome. In certain embodiments, the reference or control subject may be the same or a different subject. For example, a baseline or reference value can be determined from an analysis of the same subject at different time points and/or based upon the analysis of other comparable subjects. For example, a reference or control value could be based on the analysis of samples taking from subjects sharing one or more of gender, age, weight, disorder, medication or the like.

The sample used for detecting or determining the presence or level of MG53 is typically whole blood, plasma, serum, saliva, urine, stool (i.e., feces), tears, and any other bodily fluid, or a tissue sample (i.e., biopsy) such as a small intestine or colon sample. Preferably, the sample is serum, whole blood, plasma, stool, urine, or a tissue biopsy. In certain instances, the method of the present invention further comprises obtaining the sample from the individual prior to detecting or determining the presence or level of the marker in the sample.

In certain aspects, the methods as described herein may comprise a step diagnosing and/or monitoring a disease or disorder, wherein an increase or decrease in MG53 over a reference or a control value is indicative of a disease, disorder or syndrome. In certain embodiments, the methods as described herein may additionally comprise a further step of initiating or modifying a therapeutic regimen based upon the results of the diagnostic comparison performed as described.

In another aspect, the disclosure provides methods for determining whether an agent or combination of agents can be used to treat or ameliorate a disease or disorder, e.g., tissue injury or a muscle-related disease or disorder, comprising the steps of: a) isolating or obtaining a biological fluid sample, e.g., blood or serum, from a subject to be tested (i.e., "test sample"), wherein the subject has received treatment with an agent or combination of agents; b) determining whether the test sample contains MG53; c) comparing the test sample to a reference or control biological fluid sample from the same or a different subject (i.e., "reference sample"), and c) identifying that the agent is or is not appropriate to treat the disease or disorder based on the presence and/or amount of MG53 in the test sample. In step (c), an agent can be identified as being appropriate to treat or ameliorate a disease or disorder when the presence and/or amount of MG53 in the test sample is decreased. Alternatively, in step (c), an agent can be identified as not being appropriate to treat or ameliorate a disease or disorder when the presence and/or amount of MG53 in the test sample is increased.

In another embodiment, the description provides a method for determining whether treatment with an agent should be continued in a subject, comprising the steps of: a) isolating or obtaining two or more biological fluid samples from a subject at different times during the course of agent treatment; b) determining the presence and/or amount of MG53 in the two or more samples; and c) continuing the treatment when the level of MG53 does not increase or is decreased during the course of treatment. Alternatively, in step (c), the treatment is discontinued when the level of MG53 is increased during the course of treatment.

In another embodiment, the description provides a method for screening agents or combinations of agents for treating a disease or disorder related to tissue injury or a muscle-related disease or disorder comprising the steps of: a) isolating or obtaining a biological fluid sample, e.g., blood or serum, from a subject to be tested (i.e., "test sample"), wherein the subject has received treatment with an agent or combination of agents; b) determining whether the test sample contains MG53; c) comparing the test sample to a reference or control biological fluid sample from the same or a different subject (i.e., "reference sample"), and c) identifying that the agent is or is not appropriate to treat the disease or disorder based on the presence and/or amount of MG53 in the test sample. In step (c), an agent can be identified as being appropriate to treat or ameliorate a disease or disorder when the presence and/or amount of MG53 in the test sample is decreased.

Eccentric exercise is known to increase membrane damage in various skeletal muscles. In another aspect, the description provides methods of determining the functional status or exercise capacity of muscle in a subject comprising the steps of: a) subjecting the subject to exercise regimen; b) obtaining two or more biological tissue or fluid samples, e.g., muscle, blood and/or serum, from the subject at different times during the course of the exercise regimen; b) determining the presence and/or amount of MG53 in the two or more samples; c) comparing the presence and/or amount of MG53 in the two or more samples; and d) identifying the functional status or exercise capacity of the subject. In certain embodiment, the exercise regimen is downhill treadmill running for between 30 minutes and two hours.

Another stress that can produce extensive membrane damage in the target organ is I/R injury in the heart. Thus, in another aspect, the description provides methods of determining the functional status of the heart in a subject in response to potential I/R injury comprising the steps of: a) isolating or obtaining a biological tissue or fluid sample, e.g., heart muscle, blood and/or serum, from a subject before, during, and/or after undergoing cardiac reperfusion; b) determining the presence and/or amount of MG53 in the sample or samples; c) comparing the presence and/or amount of MG53 in the sample or samples; and d) identifying the functional status of the heart in the subject in response to ischemic reperfusion.

In any of the aspects and/or embodiments described herein, the tissue may comprise a muscle tissue, blood or serum from a subject. The term "individual," "subject," or "patient" typically refers to humans, but also to other animals including, e.g., other primates, rodents, canines, felines, equines, ovines, porcines, and the like. In any of the embodiments described herein the subject is a mammal. In still additional embodiments, the subject is a human.

In certain embodiments, the disease, disorder or syndrome may be, e.g., muscular dystrophy, cardiac ischemia, heart failure, age-related tissue degeneration, neurodegeneration, sepsis, bacterial infection, gingivitis, gum recession, periodontal disease, wrinkle protection, dermal abrasion, UV damage, nitrogen mustard (chemical blistering agents), ulcer, acute lung injury, ARDS, COPD, cardiovascular disease, cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve disease, hypercoagulation, hemophilia, wounds, lesions, cuts, abrasions, oxidative damage, surgically related lesions, burns, muscle disorders, muscle weakness, muscle atrophy, muscular dystrophy, connective tissue disorders, idiopathic thrombocytopenic purpura, secondary pathologies caused by heart failure and hypertension, hypotension, angina pectoris, myocardial infarction, tuberous sclerosis, scleroderma, transplantation, autoimmune disease, lupus erythematosus, viral/bacterial/parasitic infections, multiple sclerosis, autoimmune disease, allergies, immunodeficiencies, graft versus host disease, Th1 inflammatory diseases such as rheumatoid arthritis, multiple sclerosis, inflammatory bowel diseases, AIDS, bed sores, mucositis, eczema or dermatitis, dry skin, obesity, diabetes, endocrine disorders, anorexia, bulimia, renal artery stenosis, interstitial nephritis, glomerulonephritis, polycystic kidney disease, systemic, renal tubular acidosis, IgA nephropathy, nephrological disesases, hypercalceimia, Lesch-Nyhan syndrome, Von Hippel-Lindau (VHL) syndrome, trauma, Hirschsprung's disease, Crohn's Disease, appendicitis, endometriosis, laryngitis, psoriasis, actinic keratosis, myasthenia gravis, alpha-mannosidosis, beta-mannosidosis, other storage disorders, peroxisomal disorders such as zellweger syndrome, infantile refsum disease, rhizomelic chondrodysplasia (chondrodysplasia punctata, rhizomelic), and hyperpipecolic acidemia, osteoporosis, Albright Hereditary Osteoedystrophy, Alzheimer's disease, stroke, Parkinson's disease, Huntington's disease, cerebral palsy, epilepsy, pain, cancers, and/or other pathologies and disorders of the like.

In the methods described herein, a comparison is made between the presence and/or amount of MG53 in one or more test and/or reference samples, wherein an increase or decrease in the presence and/or amount of MG53 is indicative of a change in the status or health of the subject. In certain embodiments, the comparison is based upon a change in the absolute level of the protein.

As an alternative to making determinations based on the absolute level of a protein, determinations may be based on the normalized levels. Levels are normalized by correcting the absolute level of a protein by comparing its level to the level of a protein that does not vary with the disorder or treatment, e.g., a housekeeping protein that is constitutively expressed. This normalization allows one to compare the level in one sample to another sample or between samples from different sources.

Alternatively, the protein level can be provided as a relative level. To determine a relative level of a protein, the level of the protein is determined for 10 or more samples, preferably 50 or more samples, prior to the determination of the level for the sample in question. The mean level of the protein assayed in the larger number of samples is determined and this is used as a baseline level for the sample in question. The level of the protein determined for the test sample (absolute level) is then divided by the mean value obtained. This provides a relative level and aids in identifying changes in protein level. In addition, as more data is accumulated, the mean value can be revised, providing improved relative values based on accumulated data.

In a preferred embodiment, the description provides a method for diagnosing and/or monitoring a muscle tissue injury, and/or exercise capacity, and/or muscle-related disease or disorder in a subject comprising the steps of a) isolating or obtaining from at least one time point, a biological fluid sample selected from the group consisting of whole blood, plasma, serum, and a combination thereof, from a subject to be tested ("test sample"); b) determining the presence and/or amount of MG53 in the test sample; c) comparing the presence and/or amount of MG53 in the test sample to a reference or control sample; and d) identifying whether the subject has a muscle tissue injury, and/or a change in exercise capacity, and/or a muscle-related disease or disorder. In additional embodiments, the method further comprises a step after (d) of initiating or modifying a therapeutic or exercise regimen.

In certain embodiments, an increase in the presence and/or amount of MG53 relative to a reference or control sample is indicative of a muscle tissue injury or muscle-related disease or disorder.

In additional embodiments, a decrease in the presence and/or amount of MG53 relative to a reference or control sample is indicative of a muscle tissue injury or muscle-related disease or disorder.

In certain embodiments, an increase in the presence and/or amount of MG53 relative to a reference or control sample is indicative of the capacity for a subject to maintain exercise training.

In additional embodiments, a decrease in the presence and/or amount of MG53 relative to a reference or control sample is indicative of indicative of the capacity for a subject to maintain exercise training.

In other embodiments, a step is performed comprising obtaining a biological fluid sample selected from the group consisting of whole blood, plasma, serum, and a combination thereof, from a reference or control subject ("reference sample").

In additional embodiments, the reference or control subject is the same or different from the test subject.

In additional embodiments, the test sample is taking from two or more time points.

In certain embodiments, the biological fluid sample is whole blood or serum.

In other embodiments, the muscle tissue injury or muscle-related disease or disorder is selected from the group consisting of exercise-related tissue injury, age-related muscle degeneration, ischemic reperfusion injury, muscular dystrophy, and combinations thereof.

Isolated Proteins and Antibodies

In additional aspects, the description provides MG53 proteins; nucleic acids encoding MG53 proteins, including vectors and host cells comprising the same; as well as agents, e.g., probes, capable of specifically binding to MG53 and/or portions thereof or both. In certain embodiments, the agent or probe is an anti-MG53 antibody, portion or fragment thereof capable of specifically binding to MG53 and/or a portion thereof. In still additional embodiments, the description provides nucleic acids encoding recombinant anti-MG53 antibodies or fragments thereof, including vectors and host cells (e.g., hybridomas) comprising the same.

Thus, one aspect of the invention pertains to isolated proteins which correspond to individual markers of the invention, and biologically active portions thereof, as well as polypeptide fragments suitable for use as immunogens to raise antibodies directed against a polypeptide corresponding to a marker of the invention. In one embodiment, the native polypeptide corresponding to a marker can be isolated from cells or tissue sources by an appropriate purification scheme using standard protein purification techniques. In another embodiment, polypeptides corresponding to a marker of the invention are produced by recombinant DNA techniques. Alternative to recombinant expression, a polypeptide corresponding to a marker of the invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a polypeptide corresponding to a marker of the invention include polypeptides comprising amino acid sequences sufficiently identical to or derived from the amino acid sequence of the protein corresponding to the marker, which include fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have the amino acid sequence listed in the one of SEQ ID NOs: 1, 3, or 5-13 described herein. Other useful proteins are substantially identical (e.g., at least about 40%, preferably 50%, 60%, 70%, 80%, 90%, 95%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the NBLAST and XBLAST programs of Altschul, et al. (1990) J. Mol. Biol. 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) Nucleic Acids Res. 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) Proc. Natl. Acad. Sci. USA 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The invention also provides chimeric or fusion proteins corresponding to a marker of the invention. As used herein, a "chimeric protein" or "fusion protein" comprises all or part (preferably a biologically active part) of a polypeptide corresponding to a marker of the invention operably linked to a heterologous polypeptide (i.e., a polypeptide other than the polypeptide corresponding to the marker). Within the fusion protein, the term "operably linked" is intended to indicate that the polypeptide of the invention and the heterologous polypeptide are fused in-frame to each other. The heterologous polypeptide can be fused to the amino-terminus or the carboxyl-terminus of the polypeptide of the invention.

Useful fusion proteins include maltose binding protein and/or GST fusion protein in which a polypeptide corresponding to a marker of the invention is fused to the carboxyl terminus of the MBP or GST sequence, respectively. Such fusion proteins can facilitate the purification of a recombinant polypeptide of the invention.

In another embodiment, the fusion protein contains a heterologous signal sequence at its amino terminus. For example, the native signal sequence of a polypeptide corresponding to a marker of the invention can be removed and replaced with a signal sequence from another protein. For example, the gp67 secretory sequence of the baculovirus envelope protein can be used as a heterologous signal sequence (Ausubel et al., ed., Current Protocols in Molecular Biology, John Wiley & Sons, NY, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a polypeptide corresponding to a marker of the invention is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a polypeptide of the invention. Inhibition of ligand/receptor interaction can be useful therapeutically, both for treating proliferative and differentiative disorders and for modulating (e.g. promoting or inhibiting) cell survival. Moreover, the immunoglobulin fusion proteins of the invention can be used as immunogens to produce antibodies directed against a polypeptide of the invention in a subject, to purify ligands and in screening assays to identify molecules which inhibit the interaction of receptors with ligands.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a MBP domain.

The present invention also pertains to variants of the polypeptides corresponding to individual markers of the invention. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang, 1983, Tetrahedron 39:3; Itakura et al., 1984, Annu Rev. Biochem. 53:323; Itakura et al., 1984, Science 198:1056; Ike et al., 1983 Nucleic Acid Res. 11:477).

In addition, libraries of fragments of the coding sequence of a polypeptide corresponding to a marker of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan, 1992, Proc. Natl. Acad. Sci. USA 89:7811-7815; Delgrave et al., 1993, Protein Engineering 6(3):327-331).

An isolated polypeptide corresponding to a marker of the invention, or a fragment thereof, can be used as an immunogen to generate antibodies using standard techniques for polyclonal and monoclonal antibody preparation. The full-length polypeptide or protein can be used or, alternatively, the invention provides antigenic peptide fragments for use as immunogens. The antigenic peptide of a protein of the invention comprises at least 8 (preferably 10, 15, 20, or 30 or more) amino acid residues of the amino acid sequence of one of the polypeptides of the invention, and encompasses an epitope of the protein such that an antibody raised against the peptide forms a specific immune complex with a marker of the invention to which the protein corresponds. Preferred epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions.

As described herein, immunoassays including but not limited to enzyme-linked immunosorbent assays, radioimmunoassays and quantitative western analysis, can be useful in the diagnostic methods of the invention. Such assays rely on one or more antibodies, for example, anti-.MG53 antibodies.

An immunogen typically is used to prepare antibodies by immunizing a suitable (i e immunocompetent) subject such as a rabbit, goat, mouse, or other mammal or vertebrate. An appropriate immunogenic preparation can contain, for example, recombinantly-expressed or chemically-synthesized polypeptide. The preparation can further include an adjuvant, such as Freund's complete or incomplete adjuvant, or a similar immunostimulatory agent.

Accordingly, another aspect of the invention pertains to antibodies directed against a polypeptide of the invention. The terms "antibody" and "antibody substance" as used interchangeably herein refer to immunoglobulin molecules and immunologically active portions of immunoglobulin molecules, i.e., molecules that contain an antigen binding site which specifically binds an antigen, such as a polypeptide of the invention, e.g., an epitope of a polypeptide of the invention. A molecule which specifically binds to a given polypeptide of the invention is a molecule which binds the polypeptide, but does not substantially bind other molecules in a sample, e.g., a biological sample, which naturally contains the polypeptide.

Unless stated differently, the term "antibody" is used in its broadest sense to include one or a population of polyclonal and/or monoclonal antibodies, as well as polypeptide fragments of antibodies that retain binding activity for an MG53 epitope of at least about $1\times10^5$ M$^{-1}$. The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope.

The term antibody, as used herein, also encompasses non-naturally occurring antibodies and fragments containing, at a minimum, one $V_H$ and one $V_L$ domain, such as chimeric antibodies, humanized antibodies, fully human antibodies, domain antibodies, and single chain Fv fragments (scFv) that specifically bind MG53. For example, an immunologically active fragments of an immunoglobulin molecule known in the art as Fab, Fab' or F(ab')$_2$, which can be generated by treating the antibody with an enzyme such as pepsin, are included within the meaning of the term antibody. Such non-naturally occurring antibodies can be constructed using solid phase peptide synthesis, produced recombinantly or obtained, for example, by screening combinatorial libraries consisting of variable heavy chains and variable light chains as described by Borrebaeck (Ed.), Antibody Engineering (Second edition) New York: Oxford University Press (1995). Methods of preparing monoclonal and polyclonal antibodies are routine in the art.

Polyclonal antibodies can be prepared as described above by immunizing a suitable subject with a polypeptide of the invention as an immunogen. Preferred polyclonal antibody compositions are ones that have been selected for antibodies directed against a polypeptide or polypeptides of the invention. Particularly preferred polyclonal antibody preparations are ones that contain only antibodies directed against a polypeptide or polypeptides of the invention. Particularly preferred immunogen compositions are those that contain no other human proteins such as, for example, immunogen compositions made using a non-human host cell for recombinant expression of a polypeptide of the invention. In such a manner, the only human epitope or epitopes recognized by the resulting antibody compositions raised against this immunogen will be present as part of a polypeptide or polypeptides of the invention.

The antibody titer in the immunized subject can be monitored over time by standard techniques, such as with an enzyme linked immunosorbent assay (ELISA) using immobilized polypeptide. If desired, the antibody molecules can be harvested or isolated from the subject (e.g., from the blood or serum of the subject) and further purified by well-known techniques, such as protein A chromatography to obtain the IgG fraction. Alternatively, antibodies specific for a protein or polypeptide of the invention can be selected or (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those of the desired protein or polypeptide of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein or polypeptide of the invention.

At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975) Nature 256:495-497, the human B cell hybridoma technique (see Kozbor et al., 1983, Immunol. Today 4:72), the EBV-hybridoma technique (see Cole et al., pp. 77-96 In Monoclonal Antibodies and Cancer Therapy, Alan R. Liss, Inc., 1985) or trioma techniques. The technology for producing hybridomas is well known (see generally Current Protocols in Immunology, Coligan et al. ed., John Wiley & Sons, New York, 1994). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370-1372; Hay et al. (1992) Hum. Antibod. Hybridomas 3:81-85; Huse et al. (1989) Science 246: 1275-1281; Griffiths et al. (1993) EMBO J. 12:725-734.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041-1043; Liu et al. (1987) Proc. Natl. Acad. Sci. USA 84:3439-3443; Liu et al. (1987) J.

Immunol. 139:3521-3526; Sun et al. (1987) Proc. Natl. Acad. Sci. USA 84:214-218; Nishimura et al. (1987) Cancer Res. 47:999-1005; Wood et al. (1985) Nature 314:446-449; and Shaw et al. (1988) J. Natl. Cancer Inst. 80:1553-1559); Morrison (1985) Science 229:1202-1207; Oi et al. (1986) Bio/Techniques 4:214; U.S. Pat. No. 5,225,539; Jones et al. (1986) Nature 321:552-525; Verhoeyan et al (1988) Science 239:1534; and Beidler et al. (1988) J. Immunol. 141:4053-4060.

Antibodies of the invention may be used as therapeutic agents in treating cancers. In a preferred embodiment, completely human antibodies of the invention are used for therapeutic treatment of human cancer patients, particularly those having an ovarian cancer. Such antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide corresponding to a marker of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995) Int. Rev. Immunol. 13:65-93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope (Jespers et al., 1994, Bio/technology 12:899-903).

An antibody directed against a polypeptide corresponding to a marker of the invention (e.g., a monoclonal antibody) can be used to isolate the polypeptide by standard techniques, such as affinity chromatography or immunoprecipitation. Moreover, such an antibody can be used to detect the marker (e.g., in a cellular lysate or cell supernatant) in order to evaluate the level and pattern of expression of the marker. The antibodies can also be used diagnostically to monitor protein levels in tissues or body fluids (e.g. in an ovary-associated body fluid) as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, .beta.-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Further, an antibody (or fragment thereof) can be conjugated to a therapeutic moiety. The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Alternatively, an antibody can be conjugated to a second antibody to form an antibody heteroconjugate as described by Segal in U.S. Pat. No. 4,676,980.

Accordingly, in one aspect, the invention provides substantially purified antibodies or fragments thereof, and non-human antibodies or fragments thereof, which antibodies or fragments specifically bind to a polypeptide comprising an amino acid sequence selected from the group consisting of the amino acid sequences of the present invention, an amino acid sequence encoded by the cDNA of the present invention, a fragment of at least 15 amino acid residues of an amino acid sequence of the present invention, an amino acid sequence which is at least 95% identical to the amino acid sequence of the present invention (wherein the percent identity is determined using the ALIGN program of the GCG software package with a PAM120 weight residue table, a gap length penalty of 12, and a gap penalty of 4) and an amino acid sequence which is encoded by a nucleic acid molecule which hybridizes to a nucleic acid molecule consisting of the nucleic acid molecules of the present invention, or a complement thereof, under conditions of hybridization of 6.times.SSC at 45 .quadrature.C and washing in 0.2.times.SSC, 0.1% SDS at 65 .quadrature.C. In various embodiments, the substantially purified antibodies of the invention, or fragments thereof, can be human, non-human, chimeric and/or humanized antibodies.

In another aspect, the invention provides non-human antibodies or fragments thereof, which antibodies or fragments specifically bind to a polypeptide comprising an amino acid sequence selected from the group consisting of: the amino acid sequence of the present invention, an amino acid sequence encoded by the cDNA of the present invention, a fragment of at least 15 amino acid residues of the amino acid sequence of the present invention, an amino acid sequence which is at least 95% identical to the amino acid sequence of the present invention (wherein the percent identity is determined using the ALIGN program of the GCG software package with a PAM120 weight residue table, a gap length penalty of 12, and a gap penalty of 4) and an amino acid sequence which is encoded by a nucleic acid molecule which hybridizes to a nucleic acid molecule consisting of the nucleic acid molecules of the present invention, or a complement thereof, under conditions of hybridization of 6.times.SSC at 45 .quadrature.C and washing in 0.2.times.SSC, 0.1% SDS at 65 .quadrature.C. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies.

In still a further aspect, the invention provides monoclonal antibodies or fragments thereof, which antibodies or fragments specifically bind to a polypeptide comprising an amino acid sequence selected from the group consisting of the amino acid sequences of the present invention, an amino acid sequence encoded by the cDNA of the present invention, a fragment of at least 15 amino acid residues of an amino acid sequence of the present invention, an amino acid sequence which is at least 95% identical to an amino acid sequence of the present invention (wherein the percent identity is determined using the ALIGN program of the GCG software package with a PAM120 weight residue table, a gap length penalty of 12, and a gap penalty of 4) and an amino acid sequence which is encoded by a nucleic acid molecule which hybridizes to a nucleic acid molecule consisting of the nucleic acid molecules of the present invention, or a complement thereof, under conditions of hybridization of 6.times.SSC at 45 .quadrature.C and washing in 0.2.times.SSC, 0.1% SDS at 65 .quadrature.C. The monoclonal antibodies can be human, humanized, chimeric and/or non-human antibodies.

The substantially purified antibodies or fragments thereof may specifically bind to a signal peptide, a secreted sequence, an extracellular domain, a transmembrane or a cytoplasmic domain or cytoplasmic membrane of a polypeptide of the invention. In a particularly preferred embodiment, the substantially purified antibodies or fragments thereof, the non-human antibodies or fragments thereof, and/or the monoclonal antibodies or fragments thereof, of the invention specifically bind to a secreted sequence or an extracellular domain of the amino acid sequences of the present invention.

Any of the antibodies of the invention can be conjugated to a therapeutic moiety or to a detectable substance. Non-limiting examples of detectable substances that can be conjugated to the antibodies of the invention are an enzyme, a prosthetic group, a fluorescent material, a luminescent material, a bioluminescent material, and a radioactive material.

Figure 4:
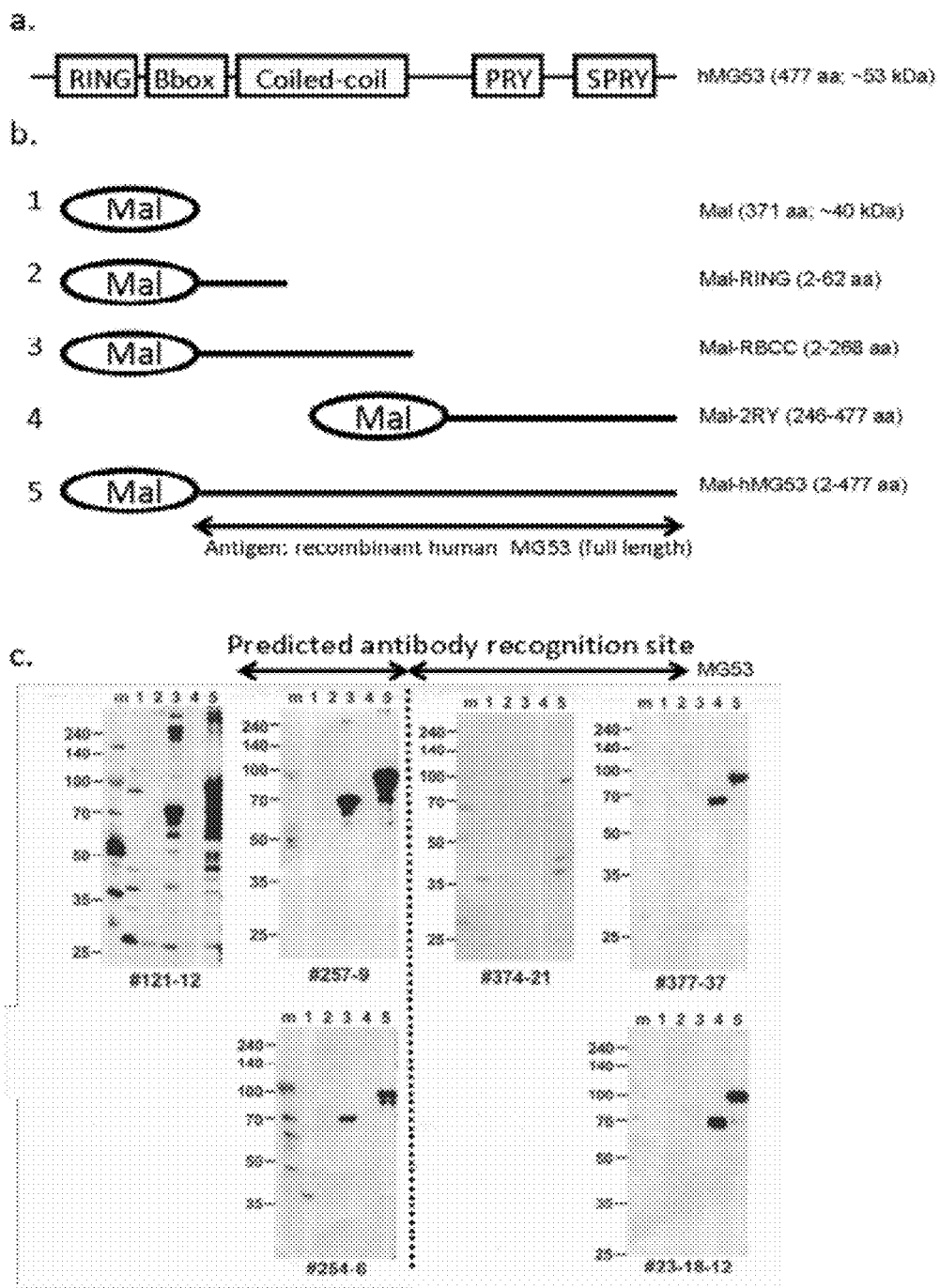
FIG. 4. Exemplary Mouse anti-human MG53 monoclonal antibodies. (a) Depicts the structural arrangement of domains in full-length human MG53 (hMG53). Human MG53 is a 477 amino acid protein that has an approximate molecular mass of 53 kDa. (b) Demonstrates exemplary maltose binding protein (Mal)-hMG53 fusion proteins that were used to generate mouse-anti-hMG53 monoclonal antibodies. At the right, the specific amino acids of hMG53 in each fusion protein is indicated (with reference to (a), Ring=includes Ring domain; RBCC=includes the Ring-Bbox-Coiled Coil domains; 2RY=includes the PRY and SPRY domains). (c) Is a Western Blot demonstrating the specificity of a number of exemplary anti-hMG53 monoclonal antibodies (i.e., antibodies from a single hybridoma cell) against microsome (m) isolated from mouse skeletal muscle, and each of the five constructs from (b) (i.e., lanes 1-5).

A variety of useful anti-MG53 antibodies are described herein. FIG. 4 demonstrates a number of exemplary Mouse anti-human MG53 monoclonal antibodies encompassed by the invention. FIG. 4a Depicts the structural arrangement of domains in full-length human MG53 (hMG53). Human MG53 is a 477 amino acid protein that has an approximate molecular mass of 53 kDa. Exemplary maltose binding protein (Mal)-hMG53 fusion proteins that were used to generate mouse-anti-hMG53 monoclonal antibodies (FIG. 4b). At the right, the specific amino acids of hMG53 in each fusion protein is indicated (with reference to (FIG. 4a), Ring=includes Ring domain; RBCC=includes the Ring-Bbox-Coiled Coil domains; 2RY=includes the PRY and SPRY domains). Western blotting demonstrates the specificity of a number of exemplary anti-hMG53 monoclonal antibodies (i.e., antibodies from a single hybridoma cell) against microsome (m) isolated from mouse skeletal muscle, and each of the five constructs from (b) (i.e., lanes 1-5) (FIG. 4c). Note that several of the monoclonal antibodies raised against human cross-react with MG53 from mouse (lane m). In addition, the figure demonstrates that monoclonal antibodies isolated from hybridomas #121-12, #254-6, and #257-9 recognize an epitope in the amino-terminus of hMG53, while antibodies from hybridomas #374-21, #377-37, and #23-18-12 recognize an epitope in the carboxyl-terminus of MG53.

In an additional aspect, the description provides kits comprising a composition as described herein and directions for performing a method as described herein. For example, in an embodiment, the description provides an anti-MG53 monoclonal antibody and/or a portion or fragment thereof, and directions for performing a diagnostic method as described herein.

In an additional aspect, the description provides a kit containing an antibody of the invention conjugated to a detectable substance, and instructions for use. Still another aspect of the invention is a pharmaceutical composition comprising an antibody of the invention and a pharmaceutically acceptable carrier. In preferred embodiments, the pharmaceutical composition contains an antibody of the invention, a therapeutic moiety, and a pharmaceutically acceptable carrier.

Still another aspect of the invention is a method of making an antibody that specifically recognizes a polypeptide of the present invention, the method comprising immunizing a mammal with a polypeptide. The polypeptide used as an immungen comprises an amino acid sequence selected from the group consisting of the amino acid sequence of the present invention, an amino acid sequence encoded by the cDNA of the nucleic acid molecules of the present invention, a fragment of at least 15 amino acid residues of the amino acid sequence of the present invention, an amino acid sequence which is at least 95% identical to the amino acid sequence of the present invention (wherein the percent identity is determined using the ALIGN program of the GCG software package with a PAM120 weight residue table, a gap length penalty of 12, and a gap penalty of 4) and an amino acid sequence which is encoded by a nucleic acid molecule which hybridizes to a nucleic acid molecule consisting of the nucleic acid molecules of the present invention, or a complement thereof, under conditions of hybridization of 6.times.SSC at 45.degree. C. and washing in 0.2.times.SSC, 0.1% SDS at 65.degree. C.

After immunization, a sample is collected from the mammal that contains an antibody that specifically recognizes the polypeptide. Preferably, the polypeptide is recombinantly produced using a non-human host cell. Optionally, the antibodies can be further purified from the sample using techniques well known to those of skill in the art. The method can further comprise producing a monoclonal antibody-producing cell from the cells of the mammal. Optionally, antibodies are collected from the antibody-producing cell.

Recombinant Expression Vectors and Host Cells

Another aspect of the invention pertains to vectors, preferably expression vectors, containing a nucleic acid encoding a polypeptide corresponding to a marker of the invention (or a portion of such a polypeptide). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Methods in Enzymology: Gene Expression Technology vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide corresponding to a marker of the invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc.; Smith and Johnson, 1988, Gene 67:31-40), pMAL (New England Bio labs, Beverly, Mass.) and pRIT5 (Pharmacia, Piscataway, N.J.) which fuse glutathione 5-transferase (GST), maltose E binding protein, or protein A, respectively, to the target recombinant protein.

Examples of suitable inducible non-fusion *E. coli* expression vectors include pTrc (Amann et al., 1988, Gene 69:301-315) and pET 11d (Studier et al., p. 60-89, In Gene Expression Technology Methods in Enzymology vol. 185, Academic Press, San Diego, Calif., 1991). Target gene expression from the pTrc vector relies on host RNA polymerase transcription from a hybrid trp-lac fusion promoter. Target gene expression from the pET 11d vector relies on transcription from a T7 gnl0-lac fusion promoter mediated by a co-expressed viral RNA polymerase (T7 gnl). This viral polymerase is supplied by host strains BL21(DE3) or HMS174(DE3) from a resident prophage harboring a T7 gnl gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, p. 119-128, In Gene Expression Technology: Methods in Enzymology vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, Nucleic Acids Res. 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari et al., 1987, EMBO J. 6:229-234), pMFa (Kurjan and Herskowitz, 1982, Cell 30:933-943), pJRY88 (Schultz et al., 1987, Gene 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, Mol. Cell Biol. 3:2156-2165) and the pVL series (Lucklow and Summers, 1989, Virology 170:31-39).

In yet another embodiment, a nucleic acid of the invention is expressed in mammalian cells using a mammalian expression vector. Examples of mammalian expression vectors include pCDM8 (Seed, 1987, Nature 329:840) and pMT2PC (Kaufman et al., 1987, EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, Genes Dev. 1:268-277), lymphoid-specific promoters (Calame and Eaton, 1988, Adv. Immunol. 43:235-275), in particular promoters of T cell receptors (Winoto and Baltimore, 1989, EMBO J. 8:729-733) and immunoglobulins (Banerji et al., 1983, Cell 33:729-740; Queen and Baltimore, 1983, Cell 33:741-748), neuron-specific promoters (e.g., the neurofilament promoter; Byrne and Ruddle, 1989, Proc. Natl. Acad. Sci. USA 86:5473-5477), pancreas-specific promoters (Edlund et al., 1985, Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, Science 249:374-379) and the .alpha.-fetoprotein promoter (Camper and Tilghman, 1989, Genes Dev. 3:537-546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., 1986, Trends in Genetics, Vol. 1(1).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., E. coli) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce a polypeptide corresponding to a marker of the invention. Accordingly, the invention further provides methods for producing a polypeptide corresponding to a marker of the invention using the host cells of the invention. In one embodiment, the method comprises culturing the host cell of invention (into which a recombinant expression vector encoding a polypeptide of the invention has been introduced) in a suitable medium such that the marker is produced. In another embodiment, the method further comprises isolating the marker polypeptide from the medium or the host cell.

The host cells of the invention can also be used to produce nonhuman transgenic animals. For example, in one embodiment, a host cell of the invention is a fertilized oocyte or an embryonic stem cell into which a sequences encoding a polypeptide corresponding to a marker of the invention have been introduced. Such host cells can then be used to create non-human transgenic animals in which exogenous sequences encoding a marker protein of the invention have been introduced into their genome or homologous recombinant animals in which endogenous gene(s) encoding a polypeptide corresponding to a marker of the invention sequences have been altered. Such animals are useful for studying the function and/or activity of the polypeptide corresponding to the marker and for identifying and/or evaluating modulators of polypeptide activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a nucleic acid encoding a polypeptide corresponding to a marker of the invention into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, Manipulating the Mouse Embryo, Cold Spring Harbor Laboratory Press, Cold Spring Harbor, N.Y., 1986. Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which contains at least a portion of a gene encoding a polypeptide corresponding to a marker of the invention into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi, 1987, Cell 51:503 for a description of homologous recombination vectors). The vector is introduced into an embryonic stem cell line (e.g., by electroporation) and cells in which the introduced gene has homologously recombined with the endogenous gene are selected (see, e.g., Li et al., 1992, Cell 69:915). The selected cells are then injected into a blastocyst of an animal (e.g., a mouse) to form aggregation chimeras (see, e.g., Bradley, Teratocarcinomas and Embryonic Stem Cells: A Practical Approach, Robertson, Ed., IRL, Oxford, 1987, pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Bio/Technology 2:823-829 and in PCT Publication NOS. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232-6236. Another example of a recombinase system is the FLP recombinase system of *Saccharomyces cerevisiae* (O'Gorman et al., 1991, Science 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810-813 and PCT Publication NOS. WO 97/07668 and WO 97/07669.

The invention also provides methods (also referred to herein as "screening assays") for identifying modulators, i.e., candidate or test compounds or agents (e.g., peptides, peptidomimetics, peptoids, small molecules or other drugs) which (a) bind to the marker, or (b) have a modulatory (e.g., stimulatory or inhibitory) effect on the activity of the marker or, more specifically, (c) have a modulatory effect on the interactions of the marker with one or more of its natural substrates (e.g., peptide, protein, hormone, co-factor, or nucleic acid), or (d) have a modulatory effect on the expression of the marker. Such assays typically comprise a reaction between the marker and one or more assay components. The other components may be either the test compound itself, or a combination of test compound and a natural binding partner of the marker.

The test compounds of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, J. Med. Chem. 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria and/or spores, (Ladner, U.S. Pat. No. 5,223,409), plasmids (Cull et al, 1992, Proc Natl Acad Sci USA 89:1865-1869) or on phage (Scott and Smith, 1990, Science 249:386-390; Devlin, 1990, Science 249:404-406; Cwirla et al, 1990, Proc. Natl. Acad. Sci. 87:6378-6382; Felici, 1991, J. Mol. Biol. 222:301-310; Ladner, supra.).

In one embodiment, the invention provides assays for screening candidate or test compounds which are substrates of a marker or biologically active portion thereof. In another embodiment, the invention provides assays for screening candidate or test compounds which bind to a marker or biologically active portion thereof. Determining the ability of the test compound to directly bind to a marker can be accomplished, for example, by coupling the compound with a radioisotope or enzymatic label such that binding of the compound to the marker can be determined by detecting the labeled marker compound in a complex. For example, compounds (e.g., marker substrates) can be labeled with $^{125}I$, $^{35}S$, $^{14}C$, or $^{3}H$, either directly or indirectly, and the radioisotope detected by direct counting of radioemission or by scintillation counting. Alternatively, assay components can be enzymatically labeled with, for example, horseradish peroxidase, alkaline phosphatase, or luciferase, and the enzymatic label detected by determination of conversion of an appropriate substrate to product.

In another embodiment, the invention provides assays for screening candidate or test compounds which modulate the activity of a marker or a biologically active portion thereof. In all likelihood, the marker can, in vivo, interact with one or more molecules, such as but not limited to, peptides, proteins, hormones, cofactors and nucleic acids. For the purposes of this discussion, such cellular and extracellular molecules are referred to herein as "binding partners" or marker "substrate".

One necessary embodiment of the invention in order to facilitate such screening is the use of the marker to identify its natural in vivo binding partners. There are many ways to accomplish this which are known to one skilled in the art. One example is the use of the marker protein as "bait protein" in a two-hybrid assay or three-hybrid assay (see, e.g., U.S. Pat. No. 5,283,317; Zervos et al, 1993, Cell 72:223-232; Madura et al, 1993, J. Biol. Chem. 268:12046-12054; Bartel et al., 1993, Biotechniques 14:920-924; Iwabuchi et al, 1993 Oncogene 8:1693-1696; Brent WO94/10300) in order to identify other proteins which bind to or interact with the marker (binding partners) and, therefore, are possibly involved in the natural function of the marker. Such marker binding partners are also likely to be involved in the propagation of signals by the marker or downstream elements of a marker-mediated signaling pathway. Alternatively, such marker binding partners may also be found to be inhibitors of the marker.

The two-hybrid system is based on the modular nature of most transcription factors, which consist of separable DNA-binding and activation domains. Briefly, the assay utilizes two different DNA constructs. In one construct, the gene that encodes a marker protein fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a marker-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be readily detected and cell colonies containing the functional transcription factor can be isolated and used to obtain the cloned gene which encodes the protein which interacts with the marker protein.

In a further embodiment, assays may be devised through the use of the invention for the purpose of identifying compounds which modulate (e.g., affect either positively or negatively) interactions between a marker and its substrates and/or binding partners. Such compounds can include, but are not limited to, molecules such as antibodies, peptides, hormones, oligonucleotides, nucleic acids, and analogs thereof. Such compounds may also be obtained from any available source, including systematic libraries of natural and/or synthetic compounds. The preferred assay components for use in this embodiment is an ovarian cancer marker identified herein, the known binding partner and/or substrate of same, and the test compound. Test compounds can be supplied from any source.

The basic principle of the assay systems used to identify compounds that interfere with the interaction between the marker and its binding partner involves preparing a reaction mixture containing the marker and its binding partner under conditions and for a time sufficient to allow the two products to interact and bind, thus forming a complex. In order to test an agent for inhibitory activity, the reaction mixture is prepared in the presence and absence of the test compound. The test compound can be initially included in the reaction mixture, or can be added at a time subsequent to the addition of the marker and its binding partner. Control reaction mixtures are incubated without the test compound or with a placebo. The formation of any complexes between the marker and its binding partner is then detected. The formation of a complex in the control reaction, but less or no such formation in the reaction mixture containing the test compound, indicates that the compound interferes with the interaction of the marker and its binding partner. Conversely, the formation of more complex in the presence of compound than in the control reaction indicates that the compound may enhance interaction of the marker and its binding partner.

The assay for compounds that interfere with the interaction of the marker with its binding partner may be conducted in a heterogeneous or homogeneous format. Heterogeneous assays involve anchoring either the marker or its binding partner onto a solid phase and detecting complexes anchored to the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the markers and the binding partners (e.g., by competition) can be identified by conducting the reaction in the presence of the test substance, i.e., by adding the test substance to the reaction mixture prior to or simultaneously with the marker and its interactive binding partner. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the marker or its binding partner is anchored onto a solid surface or matrix, while the other corresponding non-anchored component may be labeled, either directly or indirectly. In practice, microtitre plates are often utilized for this approach. The anchored species can be immobilized by a number of methods, either non-covalent or covalent, that are typically well known to one who practices the art. Non-covalent attachment can often be accomplished simply by coating the solid surface with a solution of the marker or its binding partner and drying. Alternatively, an immobilized antibody specific for the assay component to be anchored can be used for this purpose. Such surfaces can often be prepared in advance and stored.

In related embodiments, a fusion protein can be provided which adds a domain that allows one or both of the assay components to be anchored to a matrix. For example, glutathione-S-transferase/marker fusion proteins or glutathione-S-transferase/binding partner can be adsorbed onto glutathione sepharose beads (Sigma Chemical, St. Louis, Mo.) or glutathione derivatized microtiter plates, which are then combined with the test compound or the test compound and either the non-adsorbed marker or its binding partner, and the mixture incubated under conditions conducive to complex formation (e.g., physiological conditions). Following incubation, the beads or microtiter plate wells are washed to remove any unbound assay components, the immobilized complex assessed either directly or indirectly, for example, as described above. Alternatively, the complexes can be dissociated from the matrix, and the level of marker binding or activity determined using standard techniques.

Other techniques for immobilizing proteins on matrices can also be used in the screening assays of the invention. For example, either a marker or a marker binding partner can be immobilized utilizing conjugation of biotin and streptavidin. Biotinylated marker protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the protein-immobilized surfaces can be prepared in advance and stored.

In order to conduct the assay, the corresponding partner of the immobilized assay component is exposed to the coated surface with or without the test compound. After the reaction is complete, unreacted assay components are removed (e.g., by washing) and any complexes formed will remain immobilized on the solid surface. The detection of complexes anchored on the solid surface can be accomplished in a number of ways. Where the non-immobilized component is pre-labeled, the detection of label immobilized on the surface indicates that complexes were formed. Where the non-immobilized component is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds which modulate (inhibit or enhance) complex formation or which disrupt preformed complexes can be detected.

In an alternate embodiment of the invention, a homogeneous assay may be used. This is typically a reaction, analogous to those mentioned above, which is conducted in a liquid phase in the presence or absence of the test compound. The formed complexes are then separated from unreacted components, and the amount of complex formed is determined. As mentioned for heterogeneous assay systems, the order of addition of reactants to the liquid phase can yield information about which test compounds modulate (inhibit or enhance) complex formation and which disrupt preformed complexes.

In such a homogeneous assay, the reaction products may be separated from unreacted assay components by any of a number of standard techniques, including but not limited to: differential centrifugation, chromatography, electrophoresis and immunoprecipitation. In differential centrifugation, complexes of molecules may be separated from uncomplexed molecules through a series of centrifugal steps, due to the different sedimentation equilibria of complexes based on their different sizes and densities (see, for example, Rivas, G., and Minton, A. P., Trends Biochem Sci. 1993 August; 18(8): 284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the complex as compared to the uncomplexed molecules may be exploited to differentially separate the complex from the remaining individual reactants, for example through the use of ion-exchange chromatography resins. Such resins and chromatographic techniques are well known to one skilled in the art (see, e.g., Heegnit, 1998, J. Mol. Recognit. 11:141-148; Hage and Tweed, 1997, J. Chromatogr. B. Biomed Sci. Appl., 699:499-525). Gel electrophoresis may also be employed to separate complexed molecules from unbound species (see, e.g., Ausubel et al (eds.), In: Current Protocols in Molecular Biology, J. Wiley & Sons, New York. 1999). In this technique, protein or nucleic acid complexes are separated based on size or charge, for example. In order to maintain the binding interaction during the electrophoretic process, nondenaturing gels in the absence of reducing agent are typically preferred, but conditions appropriate to the particular interactants will be well known to one skilled in the art Immunoprecipitation is another common technique utilized for the isolation of a protein-protein complex from solution (see, e.g., Ausubel et al (eds.), In: Current Protocols in Molecular Biology, J. Wiley & Sons, New York. 1999). In this technique, all proteins binding to an antibody specific to one of the binding molecules are precipitated from solution by conjugating the antibody to a polymer bead that may be readily collected by centrifugation. The bound assay components are released from the beads (through a specific proteolysis event or other technique well known in the art which will not disturb the protein-protein interaction in the complex), and a second immunoprecipitation step is performed, this time utilizing antibodies specific for the correspondingly different interacting assay component. In this manner, only formed complexes should remain attached to the beads. Variations in complex formation in both the presence and the absence of a test compound can be compared, thus offering information about the ability of the compound to modulate interactions between the marker and its binding partner.

Also within the scope of the present invention are methods for direct detection of interactions between the marker and its natural binding partner and/or a test compound in a homogeneous or heterogeneous assay system without further sample manipulation. For example, the technique of fluorescence energy transfer may be utilized (see, e.g., Lakowicz et al, U.S. Pat. No. 5,631,169; Stavrianopoulos et al, U.S. Pat. No. 4,868,103). Generally, this technique involves the addition of a fluorophore label on a first 'donor' molecule (e.g., marker or test compound) such that its emitted fluorescent energy will be absorbed by a fluorescent label on a second, 'acceptor' molecule (e.g., marker or test compound), which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter). A test substance which either enhances or hinders participation of one of the species in the preformed complex will result in the generation of a signal variant to that of background. In this way, test substances that modulate interactions between a marker and its binding partner can be identified in controlled assays.

In another embodiment, modulators of marker expression are identified in a method wherein a cell is contacted with a candidate compound and the expression of mRNA or protein, corresponding to a marker in the cell, is determined. The level of expression of mRNA or protein in the presence of the candidate compound is compared to the level of expression of mRNA or protein in the absence of the candidate compound. The candidate compound can then be identified as a modulator of marker expression based on this comparison. For example, when expression of marker mRNA or protein is greater (statistically significantly greater) in the presence of the candidate compound than in its absence, the candidate compound is identified as a stimulator of marker mRNA or protein expression. Conversely, when expression of marker mRNA or protein is less (statistically significantly less) in the presence of the candidate compound than in its absence, the candidate compound is identified as an inhibitor of marker mRNA or protein expression. The level of marker mRNA or protein expression in the cells can be determined by methods described herein for detecting marker mRNA or protein.

In another aspect, the invention pertains to a combination of two or more of the assays described herein. For example, a modulating agent can be identified using a cell-based or a cell free assay, and the ability of the agent to modulate the activity of a marker protein can be further confirmed in vivo, e.g., in a whole animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein (e.g., an marker modulating agent, an antisense marker nucleic acid molecule, a marker-specific antibody, or a marker-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

It is understood that appropriate doses of small molecule agents and protein or polypeptide agents depends upon a number of factors within the knowledge of the ordinarily skilled physician, veterinarian, or researcher. The dose(s) of these agents will vary, for example, depending upon the identity, size, and condition of the subject or sample being treated, further depending upon the route by which the composition is to be administered, if applicable, and the effect which the practitioner desires the agent to have upon the nucleic acid or polypeptide of the invention. Exemplary doses of a small molecule include milligram or microgram amounts per kilogram of subject or sample weight (e.g. about 1 microgram per kilogram to about 500 milligrams per kilogram, about 100 micrograms per kilogram to about 5 milligrams per kilogram, or about 1 microgram per kilogram to about 50 micrograms per kilogram). Exemplary doses of a protein or polypeptide include gram, milligram or microgram amounts per kilogram of subject or sample weight (e.g. about 1 microgram per kilogram to about 5 grams per kilogram, about 100 micrograms per kilogram to about 500 milligrams per kilogram, or about 1 milligram per kilogram to about 50 milligrams per kilogram). It is furthermore understood that appropriate doses of one of these agents depend upon the potency of the agent with respect to the expression or activity to be modulated. Such appropriate doses can be determined using the assays described herein. When one or more of these agents is to be administered to an animal (e.g. a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific agent employed, the age, body weight, general health, gender, and diet of the subject, the time of administration, the route of administration, the rate of excretion, any drug combination, and the degree of expression or activity to be modulated.

Pharmaceutically compatible binding agents, and/or adjuvant materials can be included as part of the composition. The tablets, pills, capsules, troches, and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The nucleic acid molecules corresponding to a marker of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al., 1994, Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

Monitoring the Effectiveness of an Agent

As discussed above, the identified marker can also be used as to assess whether a disease or disorder has become refractory to an ongoing treatment. In such a use, the invention provides methods for determining whether a treatment should be continued comprising the steps of:

a) obtaining two or more samples from a patient undergoing therapy;

b) determining the level of expression of one or more markers of the invention in the sample exposed to the agent and in a sample that is not exposed to the agent; and c) discontinuing or altering treatment when one or more markers of the invention decreases and/or when one or more markers of the invention increases.

As used herein, a patient or subject refers to any subject undergoing treatment. The preferred subject will be a human patient undergoing chemotherapy treatment.

This embodiment of the present invention relies on comparing two or more samples obtained from a patient undergoing a treatment. In general, it is preferable to obtain a first sample from the patient prior to beginning therapy and one or more samples during treatment. In such a use, a baseline prior to therapy is determined and then changes in the baseline state is monitored during the course of therapy. Alternatively, two or more successive samples obtained during treatment can be used without the need of a pre-treatment baseline sample. In such a use, the first sample obtained from the subject is used as a baseline for determining whether the marker is increasing or decreasing.

In general, when monitoring the effectiveness of a therapeutic treatment, two or more samples from the patient are examined. Preferably, three or more successively obtained samples are used, including at least one pretreatment sample.

Detection Assays

An exemplary method for detecting the presence or absence of a polypeptide or nucleic acid corresponding to a marker of the invention in a biological sample involves obtaining a biological sample from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo. For example, in vitro techniques for detection of mRNA include Northern hybridizations and in situ hybridizations. In vitro techniques for detection of a polypeptide corresponding to a marker of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide corresponding to a marker of the invention include introducing into a subject a labeled antibody directed against the polypeptide. For example, the antibody can be labeled with a radioactive marker whose presence and location in a subject can be detected by standard imaging techniques.

A general principle of such diagnostic and prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In a preferred embodiment, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S. and Urbaniczky, C., 1991, Anal. Chem. 63:2338-2345 and Szabo et al., 1995, Curr. Opin. Struct. Biol. 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P., 1993, Trends Biochem Sci. 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, J. Mol. Recognit. Winter 11(1-6):141-8; Hage, D. S., and Tweed, S. A. J Chromatogr B Biomed Sci Appl 1997 Oct. 10; 699(1-2):499-525). Gel electrophoresis may also be employed to separate complexed assay components from unbound components (see, e.g., Ausubel et al., ed., Current Protocols in Molecular Biology, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In a particular embodiment, the level of mRNA corresponding to the marker can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from ovarian cells (see, e.g., Ausubel et al., ed., Current Protocols in Molecular Biology, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

An alternative method for determining the level of mRNA corresponding to a marker of the present invention in a sample involves the process of nucleic acid amplification, e.g., by rtPCR (the experimental embodiment set forth in Mullis, 1987, U.S. Pat. No. 4,683,202), ligase chain reaction (Barany, 1991, Proc. Natl. Acad. Sci. USA, 88:189-193), self sustained sequence replication (Guatelli et al., 1990, Proc. Natl. Acad. Sci. USA 87:1874-1878), transcriptional amplification system (Kwoh et al., 1989, Proc. Natl. Acad. Sci. USA 86:1173-1177), Q-Beta Replicase (Lizardi et al., 1988, Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the ovarian cells prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-ovarian cancer sample, or between samples from different sources.

Alternatively, the expression level can be provided as a relative expression level. To determine a relative expression level of a marker, the level of expression of the marker is determined for 10 or more samples of normal versus cancer cell isolates, preferably 50 or more samples, prior to the determination of the expression level for the sample in question. The mean expression level of each of the genes assayed in the larger number of samples is determined and this is used as a baseline expression level for the marker. The expression level of the marker determined for the test sample (absolute level of expression) is then divided by the mean expression value obtained for that marker. This provides a relative expression level.

In another embodiment of the present invention, a polypeptide corresponding to a marker is detected. A preferred agent for detecting a polypeptide of the invention is an antibody capable of binding to a polypeptide corresponding to a marker of the invention, preferably an antibody with a detectable label. Antibodies can be polyclonal, or more preferably, monoclonal. An intact antibody, or a fragment thereof (e.g., Fab or F(ab').sub.2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In certain instances, the presence or level of MG53 is determined using an immunoassay or an immunohistochemical assay. A non-limiting example of an immunoassay suitable for use in the methods of the present description includes an enzyme-linked immunosorbent assay (ELISA). Examples of immunohistochemical assays suitable for use in the methods of the present description include, but are not limited to, immunofluorescence assays such as direct fluorescent antibody assays, indirect fluorescent antibody (IFA) assays, anti-complement immunofluorescence assays, and avidin-biotin immunofluorescence assays. Other types of immunohistochemical assays include immunoperoxidase assays.

MG53 can be detected by enzyme-linked immunosorbent assay (ELISA). FIG. 4 demonstrates a sandwich ELISA for detection of MG53 in mouse serum. A sandwich ELISA measures the amount of the target protein between two layers of antibodies, one coating the ELISA plate (the capture antibody) and a second antibody used to recognize the target protein for quantitative measurements (the detection antibody). In this case, we used an anti-MG53 mouse monoclonal antibody (mAb5259) as the capture antibody and an affinity purified rabbit polyclonal anti-MG53 antibody as a detection antibody. An anti-rabbit IgG antibody coupled to horse-radish peroxidase was used to develop this ELISA. This ELISA was calibrated using several concentrations of purified recombinant human MG53 protein and found to respond in a dose-dependent fashion (FIG. 5a). When we applied mouse serum to this ELISA configuration we were able to detect levels of MG53 in the serum from mdx mice (FIG. 5b), illustrating that MG53 can be efficiently detected in the serum with an ELISA approach. Importantly, we also find that the ELISA is highly specific for the detection of MG53 as serum from the MG53 knockout mouse (mg53−/−) produces the same signal as vehicle controls (PBS) in this assay. Thus, we have provided proof-of-concept that ELISA can be used to detect MG53 in serum in a quantitative and specific fashion.

Any of a variety of assays, techniques, and kits known in the art can be used to determine the presence or level of MG53 in a sample to classify whether the sample is associated with tissue injury or a muscle-related disease or disorder.

The present invention relies, in part, on determining the presence or level of at least one marker, e.g., MG53, in a sample obtained from an individual. As used herein, the term "determining the presence of at least one marker" includes determining the presence of each marker of interest by using any quantitative or qualitative assay known to one of skill in the art. In certain instances, qualitative assays that determine the presence or absence of a particular trait, variable, or biochemical or serological substance (e.g., protein or antibody) are suitable for detecting each marker of interest. In certain other instances, quantitative assays that determine the presence or absence of RNA, protein, antibody, or activity are suitable for detecting each marker of interest. As used herein, the term "determining the level of at least one marker" includes determining the level of each marker of interest by using any direct or indirect quantitative assay known to one of skill in the art. In certain instances, quantitative assays that determine, for example, the relative or absolute amount of RNA, protein, antibody, or activity are suitable for determining the level of each marker of interest. One skilled in the art will appreciate that any assay useful for determining the level of a marker is also useful for determining the presence or absence of the marker.

Flow cytometry can be used to determine the presence or level of one or more markers in a sample. Such flow cytometric assays, including bead based immunoassays, can be used to determine, e.g., antibody marker levels in the same manner as described for detecting serum antibodies to *Candida albicans* and HIV proteins (see, e.g., Bishop et al., J. Immunol. Methods, 210:79-87 (1997); McHugh et al., J. Immunol. Methods, 116:213 (1989); Scillian et al., Blood, 73:2041 (1989)).

Phage display technology for expressing a recombinant antigen specific for a marker can also be used to determine the presence or level of one or more markers in a sample. Phage particles expressing an antigen specific for, e.g., an antibody marker can be anchored, if desired, to a multi-well plate using an antibody such as an anti-phage monoclonal antibody (Felici et al., "Phage-Displayed Peptides as Tools for Characterization of Human Sera" in Abelson (Ed.), Methods in Enzymol., 267, San Diego: Academic Press, Inc. (1996)).

A variety of immunoassay techniques, including competitive and non-competitive immunoassays, can be used to determine the presence or level of one or more markers in a sample (see, e.g., Self et al, Curr. Opin. Biotechnol., 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), antigen capture ELISA, sandwich ELISA, IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence (see, e.g., Schmalzing et al., Electrophoresis, 18:2184-2193 (1997); Bao, J. Chromatogr. B. Biomed. Sci., 699:463-480 (1997)). Liposome immunoassays, such as flow-injection liposome immunoassays and liposome immunosensors, are also suitable for use in the present invention (see, e.g., Rongen et al., J. Immunol. Methods, 204:105-133 (1997)). In addition, nephelometry assays, in which the formation of protein/antibody complexes results in increased light scatter that is converted to a peak rate signal as a function of the marker concentration, are suitable for use in the present invention. Nephelometry assays are commercially available from Beckman Coulter (Brea, Calif.; Kit #449430) and can be performed using a Behring Nephelometer Analyzer (Fink et al., J. Clin. Chem. Clin. Biol. Chem., 27:261-276 (1989)).

Antigen capture ELISA can be useful for determining the presence or level of one or more markers in a sample. For example, in an antigen capture ELISA, an antibody directed to a marker of interest is bound to a solid phase and sample is added such that the marker is bound by the antibody. After unbound proteins are removed by washing, the amount of bound marker can be quantitated using, e.g., a radioimmunoassay (see, e.g., Harlow and Lane, Antibodies: A Laboratory Manual, Cold Spring Harbor Laboratory, New York, 1988)). Sandwich ELISA can also be suitable for use in the present invention. For example, in a two-antibody sandwich assay, a first antibody is bound to a solid support, and the marker of interest is allowed to bind to the first antibody. The amount of the marker is quantitated by measuring the amount of a second antibody that binds the marker. The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

A radioimmunoassay using, for example, an iodine-125 ($^{125}$I) labeled secondary antibody (Harlow and Lane, supra) is also suitable for determining the presence or level of one or more markers in a sample. A secondary antibody labeled with a chemiluminescent marker can also be suitable for use in the present invention. A chemiluminescence assay using a chemiluminescent secondary antibody is suitable for sensitive, non-radioactive detection of marker levels. Such secondary antibodies can be obtained commercially from various sources, e.g., Amersham Lifesciences, Inc. (Arlington Heights, Ill.).

The immunoassays described above are particularly useful for determining the presence or level of one or more markers in a sample. An ELISA using MG53 protein or a fragment thereof is useful for determining whether a sample is positive for anti-MG53 antibodies, or for determining anti-MG53 antibody levels in a sample. An ELISA using flagellin protein or a fragment thereof is useful for determining whether a sample is positive for anti-flagellin antibodies, or for determining anti-flagellin antibody levels in a sample. In addition, the immunoassays described above are particularly useful for determining the presence or level of other markers in a sample.

Specific immunological binding of the antibody to the marker of interest can be detected directly or indirectly. Direct labels include fluorescent or luminescent tags, metals, dyes, radionuclides, and the like, attached to the antibody. An antibody labeled with iodine-125 ($^{125}$I) can be used for determining the levels of one or more markers in a sample. A chemiluminescence assay using a chemiluminescent antibody specific for the marker is suitable for sensitive, non-radioactive detection of marker levels. An antibody labeled with fluorochrome is also suitable for determining the levels of one or more markers in a sample. Examples of fluorochromes include, without limitation, DAPI, fluorescein, Hoechst 33258, R-phycocyanin, B-phycoerythrin, R-phycoerythrin, rhodamine, Texas red, and lissamine. Secondary antibodies linked to fluorochromes can be obtained commercially, e.g., goat F(ab')$_2$ anti-human IgG-FITC is available from Tago Immunologicals (Burlingame, Calif.).

Indirect labels include various enzymes well-known in the art, such as horseradish peroxidase (HRP), alkaline phosphatase (AP), •-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a •-galactosidase detection system can be used with the chromogenic substrate o-nitrophenyl-.beta.-D-galactopyranoside (ONPG), which yields a soluble product detectable at 410 nm. An urease detection system can be used with a substrate such as urea-bromocresol purple (Sigma Immunochemicals; St. Louis, Mo.). A useful secondary antibody linked to an enzyme can be obtained from a number of commercial sources, e.g., goat F(ab').sub.2 anti-human IgG-alkaline phosphatase can be purchased from Jackson ImmunoResearch (West Grove, Pa.).

A signal from the direct or indirect label can be analyzed, for example, using a spectrophotometer to detect color from a chromogenic substrate; a radiation counter to detect radiation such as a gamma counter for detection of $_{125}$I; or a fluorometer to detect fluorescence in the presence of light of a certain wavelength. For detection of enzyme-linked antibodies, a quantitative analysis of the amount of marker levels can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

Quantitative western blotting can also be used to detect or determine the presence or level of one or more markers in a sample. Western blots can be quantitated by well-known methods such as scanning densitometry or phosphorimaging. As a non-limiting example, protein samples are electrophoresed on 10% SDS-PAGE Laemmli gels. Primary murine monoclonal antibodies are reacted with the blot, and antibody binding can be confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al, J. Vasc. Surg., 28:669-675 (1998).

Alternatively, a variety of immunohistochemical assay techniques can be used to determine the presence or level of one or more markers in a sample. The term immunohistochemical assay encompasses techniques that utilize the visual detection of fluorescent dyes or enzymes coupled (i.e., conjugated) to antibodies that react with the marker of interest using fluorescent microscopy or light microscopy and includes, without limitation, direct fluorescent antibody assay, indirect fluorescent antibody (IFA) assay, anticomplement immunofluorescence, avidin-biotin immunofluorescence, and immunoperoxidase assays. An IFA assay, for example, is useful for determining whether a sample is positive for MG53. The concentration of MG53 in a sample can be quantitated, e.g., through endpoint titration or through measuring the visual intensity of fluorescence compared to a known reference standard.

Alternatively, the presence or level of a marker of interest can be determined by detecting or quantifying the amount of the purified marker. Purification of the marker can be achieved, for example, by high pressure liquid chromatography (HPLC), alone or in combination with mass spectrometry (e.g., MALDI/MS, MALDI-TOF/MS, tandem MS, etc.). Qualitative or quantitative detection of a marker of interest can also be determined by well-known methods including, without limitation, Bradford assays, Coomassie blue staining, silver staining, assays for radiolabeled protein, and mass spectrometry.

The analysis of a plurality of markers may be carried out separately or simultaneously with one test sample. For separate or sequential assay of markers, suitable apparatuses include clinical laboratory analyzers such as the ElecSys (Roche), the AxSym (Abbott), the Access (Beckman), the ADVIA®, the CENTAUR® (Bayer), and the NICHOLS ADVANTAGE® (Nichols Institute) immunoassay systems. Preferred apparatuses or protein chips perform simultaneous assays of a plurality of markers on a single surface. Particularly useful physical formats comprise surfaces having a plurality of discrete, addressable locations for the detection of a plurality of different markers. Such formats include protein microarrays, or "protein chips" (see, e.g., Ng et al., J. Cell Mol. Med., 6:329-340 (2002)) and certain capillary devices (see, e.g., U.S. Pat. No. 6,019,944). In these embodiments, each discrete surface location may comprise antibodies to immobilize one or more markers for detection at each location. Surfaces may alternatively comprise one or more discrete particles (e.g., microparticles or nanoparticles) immobilized at discrete locations of a surface, where the microparticles comprise antibodies to immobilize one or more markers for detection.

In addition to the above-described assays for determining the presence or level of various markers of interest, analysis of marker mRNA levels using routine techniques such as Northern analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. Applicable PCR amplification techniques are described in, e.g., Ausubel et al., Current Protocols in Molecular Biology, John Wiley & Sons, Inc. New York (1999), Chapter 7 and Supplement 47; Theophilus et al., "PCR Mutation Detection Protocols," Humana Press, (2002); and Innis et al., PCR Protocols, San Diego, Academic Press, Inc. (1990). General nucleic acid hybridization methods are described in Anderson, "Nucleic Acid Hybridization," BIOS Scientific Publishers, 1999. Amplification or hybridization of a plurality of transcribed nucleic acid sequences (e.g., mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Analysis of the genotype of a marker such as a genetic marker can be performed using techniques known in the art including, without limitation, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., Biotechniques, 13:626-633 (1992)), solid-phase sequencing (Zimmerman et al., Methods Mol. Cell. Biol., 3:39-42 (1992)), sequencing with mass spectrometry such as matrix-assisted laser desorption/ionization time-of-flight mass spectrometry (MALDI-TOF/MS; Fu et al., Nature Biotech., 16:381-384 (1998)), and sequencing by hybridization (Chee et al., Science, 274:610-614 (1996); Drmanac et al., Science, 260:1649-1652 (1993); Drmanac et al., Nature Biotech., 16:54-58 (1998)). Non-limiting examples of electrophoretic analysis include slab gel electrophoresis such as agarose or polyacrylamide gel electrophoresis, capillary electrophoresis, and denaturing gradient gel electrophoresis. Other methods for genotyping an individual at a polymorphic site in a marker include, e.g., the INVADER® assay from Third Wave Technologies, Inc., restriction fragment length polymorphism (RFLP) analysis, allele-specific oligonucleotide hybridization, a heteroduplex mobility assay, and single strand conformational polymorphism (SSCP) analysis.

Several markers of interest may be combined into one test for efficient processing of a multiple of samples. In addition, one skilled in the art would recognize the value of testing multiple samples (e.g., at successive time points, etc.) from the same subject. Such testing of serial samples can allow the identification of changes in marker levels over time. Increases or decreases in marker levels, as well as the absence of change in marker levels, can also provide useful information to classify or to differentiate between clinical disorders.

A panel consisting of one or more of the markers described above may be constructed to provide relevant information related to the approach of the present invention for classifying a sample as being associated with a disease or disorder, e.g., tissue injury or muscle-related disease or disorder, e.g., muscular dystrophy, or a clinical subtype thereof. Such a panel may be constructed using 1, 2, 3, 4, 5, 6, 7, 8, 9, 10, 11, 12, 13, 14, 15, 16, 17, 18, 19, 20, 25, 30, 35, 40, or more individual markers. The analysis of a single marker or subsets of markers can also be carried out by one skilled in the art in various clinical settings. These include, but are not limited to, ambulatory, urgent care, critical care, intensive care, monitoring unit, inpatient, outpatient, physician office, medical clinic, and health screening settings.

The analysis of markers could be carried out in a variety of physical formats as well. For example, the use of microtiter plates or automation could be used to facilitate the processing of large numbers of test samples. Alternatively, single sample formats could be developed to facilitate treatment and diagnosis in a timely fashion.

One skilled in the art will know many other suitable carriers for binding antibody or antigen, and will be able to adapt such support for use with the present invention. For example, protein isolated from ovarian cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

The invention also encompasses kits for detecting the presence of a polypeptide or nucleic acid corresponding to a marker of the invention in a biological sample (e.g. an ovary-associated body fluid such as a urine sample). Such kits can be used to determine if a subject is suffering from or is at increased risk of developing ovarian cancer. For example, the kit can comprise a labeled compound or agent capable of detecting a polypeptide or an mRNA encoding a polypeptide corresponding to a marker of the invention in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for interpreting the results obtained using the kit.

For antibody-based kits, the kit can comprise, for example: (1) a first antibody (e.g., attached to a solid support) which binds to a polypeptide corresponding to a marker of the invention; and, optionally, (2) a second, different antibody which binds to either the polypeptide or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

Electronic Apparatus Readable Media and Arrays

Electronic apparatus readable media comprising a marker of the present invention is also provided. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon a marker of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the markers of the present invention.

A variety of software programs and formats can be used to store the marker information of the present invention on the electronic apparatus readable medium. For example, the nucleic acid sequence corresponding to the markers can be represented in a word processing text file, formatted in commercially-available software such as WordPerfect and MicroSoft Word, or represented in the form of an ASCII file, stored in a database application, such as DB2, Sybase, Oracle, or the like, as well as in other forms. Any number of dataprocessor structuring formats (e.g., text file or database) may be employed in order to obtain or create a medium having recorded thereon the markers of the present invention.

By providing the markers of the invention in readable form, one can routinely access the marker sequence information for a variety of purposes. For example, one skilled in the art can use the nucleotide or amino acid sequences of the present invention in readable form to compare a target sequence or target structural motif with the sequence information stored within the data storage means. Search means are used to identify fragments or regions of the sequences of the invention which match a particular target sequence or target motif.

The invention also includes an array comprising a marker of the present invention. The array can be used to assay expression of one or more genes in the array. In one embodiment, the array can be used to assay gene expression in a tissue to ascertain tissue specificity of genes in the array. In this manner, up to about 36,000 genes can be simultaneously assayed for expression. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array.

The array is also useful for ascertaining the effect of the expression of a gene on the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes that could serve as a molecular target for diagnosis or therapeutic intervention.

In any of the methods as described herein, the step of determining or assaying for the presence and/or amount of MG53 may include the computer-implemented detection and/or quantification of a signal generated by the binding or interaction of an agent or probe, e.g., labeled antibody, with the target, e.g., MG53, in the sample. For example, in certain embodiments, the computer-implemented system comprises a microscope, and a computer display in communication with a computer processor. In certain embodiments, the processor is adapted to execute a process or program that measures the amount or intensity of a probe signal from one or more test samples, and quantifies it and/or compares it with one or more reference samples. In certain embodiments, the computer-implemented system is automated such that one or more samples can be processed, analyzed, and the results displayed automatically to facilitate a diagnosis by the user.

Statistical Algorithms

In some aspects, the present invention provides methods, and systems for classifying whether a sample is associated with a disease or disorder related to alterations in blood or serum levels of MG53 using a statistical algorithm or process to classify the sample as a disease sample or non-disease sample. Preferably, the statistical algorithms or processes independently comprise one or more learning statistical classifier systems. As described herein, a combination of learning statistical classifier systems advantageously provides improved sensitivity, specificity, negative predictive value, positive predictive value, and/or overall accuracy for classifying whether a sample is associated with a disease or disorder.

The term "statistical algorithm" or "statistical process" includes any of a variety of statistical analyses used to determine relationships between variables. In the present invention, the variables are the presence or level of at least one marker of interest. Any number of markers can be analyzed using a statistical algorithm described herein. For example, the presence or levels of 1, 2, 3, 4, 5, 6, 7, 8, 9, 10, 11, 12, 13, 14, 15, 16, 17, 18, 19, 20, 25, 30, 35, 40, 45, 50, or more markers can be included in a statistical algorithm. In one embodiment, logistic regression is used. In another embodiment, linear regression is used. In certain instances, the statistical algorithms of the present invention can use a quantile measurement of a particular marker within a given population as a variable. Quantiles are a set of "cut points" that divide a sample of data into groups containing (as far as possible) equal numbers of observations. For example, quartiles are values that divide a sample of data into four groups containing (as far as possible) equal numbers of observations. The lower quartile is the data value a quarter way up through the ordered data set; the upper quartile is the data value a quarter way down through the ordered data set. Quintiles are values that divide a sample of data into five groups containing (as far as possible) equal numbers of observations. The present invention can also include the use of percentile ranges of marker levels (e.g., tertiles, quartile, quintiles, etc.), or their cumulative indices (e.g., quartile sums of marker levels, etc.) as variables in the algorithms (just as with continuous variables).

Preferably, the statistical algorithms of the present invention comprise one or more learning statistical classifier systems. As used herein, the term "learning statistical classifier system" includes a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ).

Random forests are learning statistical classifier systems that are constructed using an algorithm developed by Leo Breiman and Adele Cutler. Random forests use a large number of individual decision trees and decide the class by choosing the mode (i.e., most frequently occurring) of the classes as determined by the individual trees. Random forest analysis can be performed, e.g., using the RandomForests software available from Salford Systems (San Diego, Calif.). See, e.g., Breiman, Machine Learning, 45:5-32 (2001); and http://stat-www.berkeley.edu/users/breiman/RandomForests/cc_home.htm, for a description of random forests.

Classification and regression trees represent a computer intensive alternative to fitting classical regression models and are typically used to determine the best possible model for a categorical or continuous response of interest based upon one or more predictors. Classification and regression tree analysis can be performed, e.g., using the C&RT software available from Salford Systems or the Statistica data analysis software available from StatSoft, Inc. (Tulsa, Okla.). A description of classification and regression trees is found, e.g., in Breiman et al. "Classification and Regression Trees," Chapman and Hall, New York (1984); and Steinberg et al., "CART: Tree-Structured Non-Parametric Data Analysis," Salford Systems, San Diego, (1995).

Neural networks are interconnected groups of artificial neurons that use a mathematical or computational model for information processing based on a connectionist approach to computation. Typically, neural networks are adaptive systems that change their structure based on external or internal information that flows through the network. Specific examples of neural networks include feed-forward neural networks such as perceptrons, single-layer perceptrons, multi-layer perceptrons, backpropagation networks, ADALINE networks, MADALINE networks, Learnmatrix networks, radial basis function (RBF) networks, and self-organizing maps or Kohonen self-organizing networks; recurrent neural networks such as simple recurrent networks and Hopfield networks; stochastic neural networks such as Boltzmann machines; modular neural networks such as committee of machines and associative neural networks; and other types of networks such as instantaneously trained neural networks, spiking neural networks, dynamic neural networks, and cascading neural networks. Neural network analysis can be performed, e.g., using the Statistica data analysis software available from StatSoft, Inc. See, e.g., Freeman et al., In "Neural Networks: Algorithms, Applications and Programming Techniques," Addison-Wesley Publishing Company (1991); Zadeh, Information and Control, 8:338-353 (1965); Zadeh, "IEEE Trans. on Systems, Man and Cybernetics," 3:28-44 (1973); Gersho et al., In "Vector Quantization and Signal Compression," Kluywer Academic Publishers, Boston, Dordrecht, London (1992); and Hassoun, "Fundamentals of Artificial Neural Networks," MIT Press, Cambridge, Mass., London (1995), for a description of neural networks.

Support vector machines are a set of related supervised learning techniques used for classification and regression and are described, e.g., in Cristianini et al., "An Introduction to Support Vector Machines and Other Kernel-Based Learning Methods," Cambridge University Press (2000). Support vector machine analysis can be performed, e.g., using the SVM-.sup.light software developed by Thorsten Joachims (Cornell University) or using the LIBSVM software developed by Chih-Chung Chang and Chih-Jen Lin (National Taiwan University).

The learning statistical classifier systems described herein can be trained and tested using a cohort of samples (e.g., serological samples) from healthy individuals and patients suffering from a disease or disorder, e.g., tissue injury or muscle-related disease or disorder. For example, samples from patients diagnosed by a physician, as having muscular dystrophy are suitable for use in training and testing the learning statistical classifier systems of the present invention. Samples from healthy individuals can include those that were not identified as muscular dystrophy samples. One skilled in the art will know of additional techniques and diagnostic criteria for obtaining a cohort of patient samples that can be used in training and testing the learning statistical classifier systems of the present invention.

As used herein, the term "sensitivity" refers to the probability that a diagnostic method, system, or code of the present invention gives a positive result when the sample is positive, e.g., having a muscle-related disorder, e.g., muscular dystrophy. Sensitivity is calculated as the number of true positive results divided by the sum of the true positives and false negatives. Sensitivity essentially is a measure of how well a method, system, or code of the present invention correctly identifies those with a muscle-related disorder, e.g., muscular dystrophy, from those without the disease. The statistical algorithms can be selected such that the sensitivity of classifying a muscle-related disorder, e.g., muscular dystrophy, is at least about 60%, and can be, for example, at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In preferred embodiments, the sensitivity of classifying a muscle-related disorder, e.g., muscular dystrophy, is at least about 90% when a combination of learning statistical classifier systems is used.

The term "specificity" refers to the probability that a diagnostic method, system, or code of the present invention gives a negative result when the sample is not positive, e.g., not having a muscle-related disorder, e.g., muscular dystrophy. Specificity is calculated as the number of true negative results divided by the sum of the true negatives and false positives. Specificity essentially is a measure of how well a method, system, or code of the present invention excludes those who do not have a muscle-related disorder, e.g., muscular dystrophy, from those who have the disease. The statistical algorithms can be selected such that the specificity of classifying a muscle-related disorder, e.g., muscular dystrophy, is at least about 70%, for example, at least about 75%, 80%, 85%, 86%, 87%, 88%, 89%, 90%, 91%, 92%, 93%, 94%, 95%, 96%, 97%, 98%, or 99%. In preferred embodiments, the specificity of classifying a muscle-related disorder, e.g., muscular dystrophy, is at least about 90% when a combination of learning statistical classifier systems is used.

As used herein, the term "negative predictive value" or "NPV" refers to the probability that an individual identified as not having a muscle-related disorder, e.g., muscular dystrophy, actually does not have the disease. Negative predictive value can be calculated as the number of true negatives divided by the sum of the true negatives and false negatives. Negative predictive value is determined by the characteristics of the diagnostic method, system, or code as well as the prevalence of the disease in the population analyzed. The statistical algorithms can be selected such that the negative predictive value in a population having a disease prevalence is in the range of about 70% to about 99% and can be, for example, at least about 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In preferred embodiments, the negative predictive value of classifying a muscle-related disorder, e.g., muscular dystrophy, is at least about 78% when a combination of learning statistical classifier systems is used.

The term "positive predictive value" or "PPV" refers to the probability that an individual identified as having a muscle-related disorder, e.g., muscular dystrophy, actually has the disease. Positive predictive value can be calculated as the number of true positives divided by the sum of the true positives and false positives. Positive predictive value is determined by the characteristics of the diagnostic method, system, or code as well as the prevalence of the disease in the population analyzed. The statistical algorithms can be selected such that the positive predictive value in a population having a disease prevalence is in the range of about 80% to about 99% and can be, for example, at least about 80%, 85%, 86%, 87%, 88%, 89%, 90%, 91%, 92%, 93%, 94%, 95%, 96%, 97%, 98%, or 99%. In preferred embodiments, the positive predictive value of classifying a muscle-related disorder, e.g., muscular dystrophy, is at least about 86% when a combination of learning statistical classifier systems is used.

Predictive values, including negative and positive predictive values, are influenced by the prevalence of the disease in the population analyzed. In the methods, systems, and code of the present invention, the statistical algorithms can be selected to produce a desired clinical parameter for a clinical population with a particular prevalence. For example, learning statistical classifier systems can be selected for a a muscle-related disorder, e.g., muscular dystrophy, prevalence of up to about 1%, 2%, 3%, 4%, 5%, 6%, 7%, 8%, 9%, 10%, 15%, 20%, 25%, 30%, 35%, 40%, 45%, 50%, 55%, 60%, 65%, or 70%, which can be seen, e.g., in a clinician's office such as a gastroenterologist's office or a general practitioner's office.

As used herein, the term "overall agreement" or "overall accuracy" refers to the accuracy with which a method, system, or code of the present invention classifies a disease state. Overall accuracy is calculated as the sum of the true positives and true negatives divided by the total number of sample results and is affected by the prevalence of the disease in the population analyzed. For example, the statistical algorithms can be selected such that the overall accuracy in a patient population having a disease prevalence is at least about 60%, and can be, for example, at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In preferred embodiments, the overall accuracy of classifying a muscle-related disorder, e.g., muscular dystrophy, is at least about 90% (e.g., 92%) when a combination of learning statistical classifier systems is used.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the invention described herein. Such equivalents are intended to be encompassed by the following claims.

It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

The invention claimed is:

1. A method for diagnosing and/or monitoring at least one of a muscle tissue injury, exercise capacity, muscle-related disease or disorder or combination thereof in a subject comprising the steps of:
   a) isolating or obtaining from at least one time point, a biological fluid sample selected from the group consisting of whole blood, plasma, serum, and a combination thereof, from a subject to be tested ("test sample");
   b) determining the presence and/or amount of MG53 in the test sample;
   c) comparing the presence and/or amount of MG53 in the test sample to a reference or control sample; and
   d) identifying whether the subject has at least one of a muscle tissue injury, a change in exercise capacity, a muscle-related disease or disorder or a combination thereof.

2. The method of claim 1, wherein an increase in the presence and/or amount of MG53 relative to a reference or control sample is indicative of at least one of muscle tissue injury, exercise capacity or a muscle-related disease or disorder.

3. The method of claim 1, wherein a decrease in the presence and/or amount of MG53 relative to a reference or control sample is indicative of at least one of muscle tissue injury, exercise capacity or a muscle-related disease or disorder.

4. The method of claim 1, wherein prior to step (c) a step is performed comprising isolating or obtaining a biological fluid sample selected from the group consisting of whole blood, plasma, serum, and a combination thereof, from a reference or control subject ("reference sample").

5. The method of claim 4, wherein the reference or control subject is the same or different from the test subject.

6. The method of claim 1, wherein test sample is taking from two or more time points.

7. The method of claim 1, further comprising a step after (d) of initiating or modifying a therapeutic or exercise regimen.

8. The method of claim 1, wherein the biological fluid sample is whole blood.

9. The method of claim 1, wherein the biological fluid sample is serum.

10. The method of claim 1, wherein the muscle tissue injury is at least one of exercise related, age-related muscle degeneration, ischemic reperfusion injury, trauma induced injury to skeletal or cardiac muscle or a combination thereof.

11. The method of claim 1, wherein the muscle tissue injury is ischemic reperfusion injury.

12. The method of claim 1, wherein the muscle-related disease or disorder is muscular dystrophy.

13. The method of claim 1, wherein the presence and/or amount of MG53 is determined using an anti-MG53 antibody.

14. The method of claim 1, wherein the antibody binds immunospecifically to a polypeptide having an amino acid sequence of at least one of SEQ ID NO. 1, 3, or 5-13.

15. The method of claim 13, wherein the presence and/or amount of MG53 is determined by assaying the sample with an immunoassay.

16. The method of claim 15, wherein said immunoassay is an enzyme-linked immunosorbent assay (ELISA).

17. The method of claim 13, wherein the presence and/or amount of MG53 is determined by assaying the sample with an immunohistochemical assay.

18. The method of claim 17, wherein said immunohistochemical assay is an immunofluorescence assay.

19. A method for determining whether treatment with a therapeutic agent should be continued in a subject suffering from a muscle tissue injury or a muscle-related disease or disorder comprising the steps of:
 a) isolating or obtaining from at least two time points during the course of treatment, a biological fluid sample selected from the group consisting of whole blood, plasma, serum, and a combination thereof, from a subject to be tested ("test samples");
 b) determining the presence and/or amount of MG53 in the test samples;
 c) comparing the presence and/or amount of MG53 in the test samples; and
 d) continuing the treatment when the presence and/or amount of MG53 does not increase or is decreased during the course of treatment or discontinuing the treatment when presence and/or amount of MG53 is increased during the course of treatment.

20. A method for screening agents or combinations of agents for treating muscle tissue injury or a muscle-related disease or disorder comprising the steps of:
 a) obtaining a biological fluid sample selected from the group consisting of whole blood, plasma, serum, and a combination thereof, from a subject to be tested ("test sample"), wherein the subject has received treatment with an agent or combination of agents;
 b) determining whether the test sample contains MG53;
 c) comparing the test sample to a reference or control sample from the same or a different subject; and
 c) identifying that the agent is or is not appropriate to treat the disease or disorder based on the presence and/or amount of MG53 in the test sample, wherein an agent is identified as being appropriate to treat or ameliorate a disease or disorder when the presence and/or amount of MG53 in the test sample is decreased.

\* \* \* \* \*